(12) United States Patent
Gupta

(10) Patent No.: US 10,689,689 B2
(45) Date of Patent: Jun. 23, 2020

(54) GENERIC METHOD FOR THE STABILIZATION OF SPECIFIC RNA

(71) Applicant: Roche Molecular Systems, Inc., Pleasanton, CA (US)

(72) Inventor: Amar Gupta, Danville, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 475 days.

(21) Appl. No.: 15/385,468

(22) Filed: Dec. 20, 2016

(65) Prior Publication Data
US 2017/0183720 A1 Jun. 29, 2017

Related U.S. Application Data

(60) Provisional application No. 62/271,614, filed on Dec. 28, 2015.

(51) Int. Cl.
| | | |
|---|---|---|
| *C12Q 1/6832* | (2018.01) | |
| *C12Q 1/6853* | (2018.01) | |
| *C12Q 1/6876* | (2018.01) | |
| *C12Q 1/6851* | (2018.01) | |
| *C12Q 1/6848* | (2018.01) | |

(52) U.S. Cl.
CPC ......... *C12Q 1/6832* (2013.01); *C12Q 1/6848* (2013.01); *C12Q 1/6851* (2013.01); *C12Q 1/6853* (2013.01); *C12Q 1/6876* (2013.01)

(58) Field of Classification Search
None
See application file for complete search history.

(56) References Cited

U.S. PATENT DOCUMENTS

| | | | | |
|---|---|---|---|---|
| 5,210,015 | A * | 5/1993 | Gelfand | C07H 21/00 435/18 |
| 5,861,250 | A | 1/1999 | Stanley et al. | |
| 5,939,262 | A * | 8/1999 | Pasloske | C07K 14/005 435/235.1 |
| 6,251,600 | B1 * | 6/2001 | Winger | C07H 21/00 435/6.1 |
| 6,300,056 | B1 * | 10/2001 | Irvine | C12Q 1/682 435/5 |
| 7,183,395 | B2 * | 2/2007 | Mauro | C12N 15/1048 435/320.1 |
| 2011/0009466 | A1 | 1/2011 | Schier et al. | |
| 2012/0052502 | A1 | 3/2012 | Li | |
| 2015/0232846 | A1 * | 8/2015 | Ozsolak | C12N 15/63 514/44 R |
| 2015/0267192 | A1 | 9/2015 | Heartlein et al. | |

OTHER PUBLICATIONS

International Search Report dated Apr. 6, 2017 in Application No. PCT/EP2016/082696, 9 pages.
Hoofar, J. et al., "Practical Considerations in Design of Internal Amplification Controls for Diagnostic PCR Assays", J Clin Microbiol. May 2004; 42(5): 1863-1868.
Stocher, M. et al., "A convenient approach to the generation of multiple internal control DNA for a panel of real-time PCR assays", J Virol Methods. Mar. 2003;108(1):1-8.
"Accuplex(TM) Recombinant Viral Technology". Product Sheet, 2006.

\* cited by examiner

*Primary Examiner* — Amanda Haney
(74) *Attorney, Agent, or Firm* — David J. Chang

(57) ABSTRACT

The present invention relates to methods and compositions for the stabilization of specific RNA molecules that can either be the target for detection or the control standard.

1 Claim, 6 Drawing Sheets
Specification includes a Sequence Listing.

GENERIC METHOD FOR THE STABILIZATION OF SPECIFIC RNA

CROSS REFERENCE TO RELATED APPLICATIONS

This application claims the benefit of priority of U.S. Provisional Patent Application Ser. No. 62/271,614, filed Dec. 28, 2015, which is incorporated herein by reference in its entirety.

REFERENCE TO SEQUENCE LISTING

This application contains a Sequence Listing submitted as an electronic text file named "33287_US1.txt", having a size in bytes of 20 kb, and created on Nov. 30, 2016. The information contained in this electronic file is hereby incorporated by reference in its entirety pursuant to 37 CFR § 1.52(e)(5).

FIELD OF THE INVENTION

The present invention belongs to the field of in-vitro diagnostics, and in particular to the detection and quantitation of nucleic acid through amplification technology.

BACKGROUND OF THE INVENTION

In the field of molecular diagnostics, the amplification of nucleic acids from numerous sources has been of considerable significance. Examples for diagnostic applications of nucleic acid amplification and detection are the detection of viruses such as Human Papilloma Virus (HPV), West Nile Virus (WNV) or the routine screening of blood donations for the presence of Human Immunodeficiency Virus (HIV), Hepatitis-B (HBV) and/or C Virus (HCV). Furthermore, said amplification techniques are suitable for bacterial targets such as mycobacteria, or the analysis of oncology markers.

The most prominent and widely-used amplification technique is Polymerase Chain Reaction (PCR). Other amplification reactions comprise, among others, the Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification. Automated systems for PCR-based analysis often make use of real-time detection of product amplification during the PCR process in the same reaction vessel. Key to such methods is the use of modified oligonucleotides carrying reporter groups or labels.

It is mostly desirable or even mandatory in the field of clinical nucleic acid diagnostics to control the respective amplification using control nucleic acids with a known sequence, for qualitative (performance control) and/or quantitative (determination of the quantity of a target nucleic using the control as a reference) purposes. Given the diversity especially of diagnostic targets, comprising prokaryotic, eukaryotic as well as viral nucleic acids, and given the diversity between different types of nucleic acids such as RNA and DNA, control nucleic acids are usually designed in a specific manner. In brief, these controls usually resemble the target nucleic acid for which they serve as control in order to mimic their properties during the process. This circumstance applies for both qualitative and quantitative assays. In case multiple parameters are to be detected in a single or in parallel experiments, usually different controls resembling different target nucleic acids are employed, such as e.g. in Swanson et al. (J. Clin. Microbiol., (2004), 42, pp. 1863-1868). Stocher et al. (J. Virol. Meth. (2003), 108, pp. 1-8) discloses a control nucleic acid in which multiple virus-specific competitive controls are comprised on the same DNA molecule.

In the last few years, diagnostic assays and assays for specific mRNA species have been developed based on the detection of specific nucleic acid sequences. Many of these assays have been adapted to determine the absolute concentration of a specific RNA species. These absolute quantification assays require the use of an RNA standard of which the precise amount has been previously determined. These RNA standards are usually synthesized by in vitro transcription or are the infectious agents themselves. The RNA is purified and then quantified by several different methods, such as absorbance at $OD_{260}$, phosphate analysis, hyperchromicity or isotopic tracer analysis (Collins, 1995).

Due to the inherent thermal instability of RNA and the ubiquitous sources of RNase contamination, both specific mRNA of interest and RNA used as standards are often subject to unwanted degradation during sample acquisition, storage, or other downstream processes, often resulting in testing failure or decreased sensitivity of detection.

One common method for stabilizing RNA is the so-called "armored RNA" method, where the RNA is encapsulated using the coat proteins of a bacteriophage to create pseudoviral particles (and as further described in U.S. Pat. Nos. 5,677,124 and 5,939,262, which are both hereby incorporated by reference in their entirety). Another method of encapsulation of RNA involves the AccuPlex technology (SeraCare Life Sciences, Milford Mass.) in which the RNA of interest is generated by exocytosis inside a mammalian virus envelope. However, the RNA protection offered by these encapsulated particles is limited at elevated temperatures. Clearly, there is a need for novel methods and compositions that increase the shelf life of RNA in products developed in areas where refrigeration may be limited.

SUMMARY OF THE INVENTION

The present invention relates to methods and compositions for the stabilization of specific RNA molecules that can either be the target for detection or the control standard. In one aspect, the invention relates to a method of preventing or reducing degradation of a segment of a single-stranded RNA template that is amplified in an amplification reaction, the method comprising the steps of providing the single-stranded RNA template; hybridizing the single-stranded RNA template with one or more oligonucleotides whose sequences are completely or partially complementary to the segment of the single-stranded RNA template that is amplified; and reverse transcribing and amplifying the segment of the single-stranded RNA template under reaction conditions whereby the one or more oligonucleotides do not interfere with reverse transcription and amplification and whereby the one or more oligonucleotides do not serve as primers, probes or templates during reverse transcription and amplification.

In one embodiment, each one oligonucleotide from the one or more oligonucleotides has a melting temperature that is at least 5° C. lower than an extension temperature used during amplification. In another embodiment, each one oligonucleotide from the one or more oligonucleotides has a melting temperature that is at least 5° C. lower than melting temperatures of primers and probes used during reverse transcription and amplification. In one embodiment, each one oligonucleotide from the one or more oligonucleotides is present at a concentration that is at least fifty-fold lower than the concentration of primers and probes used during reverse transcription and amplification. In another embodiment, each one oligonucleotide from the one or more oligonucleotide is present at a concentration that is between 0.1 nM and 2.0 nM. In one embodiment, the one or more oligonucleotides hybridize to more than 48% of the segment of the single-stranded RNA template that is amplified. In one embodiment, the one or more oligonucleotides hybridize to more than 60%, more than 75%, or more than 90% of the segment of the single-stranded RNA template that is amplified. In one embodiment, the one or more oligonucleotides hybridize to the entire segment of the single-stranded RNA template that is amplified. In one embodiment, each one oligonucleotide from the one or more oligonucleotides is between 11 nucleotides and 50 nucleotides or between 11 nucleotides and 40 nucleotides in length or between 11 nucleotides and 30 nucleotides in length. In another embodiment, each one oligonucleotide from the one or more oligonucleotides has a melting temperature that ranges between 20° C. and 80° C., or between 30° C. and 70° C., or between 40° C. and 60° C. or between 48° C. and 58° C. In yet another embodiment, the sequence of each one oligonucleotide from the one or more oligonucleotides does not overlap with the sequence of another oligonucleotide from the one or more oligonucleotides. In another embodiment, the single-stranded RNA template is caged. The caging may be accomplished by means of encapsulation, encapsidation, trapping, or by the RNA template being inside a cell. In another embodiment a step of isolating or purifying the single-stranded RNA template is performed prior to the step of reverse transcription and amplification. In another embodiment, the one or more oligonucleotides comprise a group of oligonucleotides whose sequences are selected from group consisting of SEQ ID NOs: 1-10, 11-19, 20-27, and 28-35.

In another aspect, the invention relates to a method of detecting the presence of a tested RNA sequence in a sample during an amplification reaction comprising obtaining the sample; obtaining a nucleic acid standard that serves as a standard in detection and/or quantification of the tested RNA sequence wherein the nucleic acid standard comprises a single-strand RNA control sequence and one or more oligonucleotide whose sequences are completely or partially complementary to a segment of the single-stranded RNA control sequence; mixing the sample and the nucleic acid standard; providing conditions for performing reverse transcription and amplification of both the tested RNA sequence and the segment of the single-stranded RNA control sequence, wherein under these conditions, the one or more oligonucleotides do not interfere with reverse transcription and amplification and whereby the one or more oligonucleotides do not serve as primers, probes or templates during reverse transcription and amplification; and detecting amplification products from the tested RNA sequence and from the single-stranded RNA control sequence.

In one embodiment, each one oligonucleotide from the one or more oligonucleotides has a melting temperature that is at least 5° C. lower than an extension temperature used during amplification. In another embodiment, each one oligonucleotide from the one or more oligonucleotides has a melting temperature that is at least 5° C. lower than melting temperatures of primers and probes used during reverse transcription and amplification. In one embodiment, each one oligonucleotide from the one or more oligonucleotides is present at a concentration that is at least fifty-fold lower than the concentration of primers and probes used during reverse transcription and amplification. In another embodiment, each one oligonucleotide from the one or more oligonucleotide is present at a concentration that is between 0.1 nM and 2.0 nM. In one embodiment, the one or more oligonucleotides hybridize to more than 48% of the segment of the single-stranded RNA control sequence. In one embodiment, the one or more oligonucleotides hybridize to more than 60%, more than 75%, or more than 90% of the segment of the single-strand RNA control sequence that is amplified. In one embodiment, the one or more oligonucleotides hybridize to the entire segment of the single-stranded RNA control sequence. In one embodiment, each one oligonucleotide from the one or more oligonucleotides is between 11 nucleotides and 50 nucleotides or between 11 nucleotides and 40 nucleotides in length or between 11 nucleotides and 30 nucleotides in length. In another embodiment, each one oligonucleotide from the one or more oligonucleotides has a melting temperature that ranges between 20° C. and 80° C., or between 30° C. and 70° C. or between 40° C. and 60° C. or between 48° C. and 58° C. In yet another embodiment, the sequence of each one oligonucleotide from the one or more oligonucleotides does not overlap with the sequence of another oligonucleotide from the one or more oligonucleotides. In one embodiment, the single-stranded RNA control sequence is caged. In some embodiments, the single-strand RNA control sequence is caged by means selected from the group consisting of encapsulation, encapsidation, trapping, and being inside a cell. In another embodiment, a step of isolating or purifying both the tested RNA sequence and the single-stranded RNA control sequence is performed prior to the step of providing conditions for performing reverse transcription and amplification. In a further embodiment, the one or more oligonucleotides comprise a group of oligonucleotides whose sequences are selected from group consisting of SEQ ID NOs: 1-10, 11-19, 20-27, and 28-35.

In another aspect, the invention relates to a nucleic acid standard that serves as a standard in detection and/or quantification of a tested RNA sequence that is amplified in an amplification reaction wherein the nucleic acid standard comprises a single-strand RNA control sequence and one or more oligonucleotide whose sequences are completely or partially complementary to a segment of the single-stranded RNA control sequence and hybridize to more than 48% of the segment of the single-stranded RNA control sequence, wherein the one or more oligonucleotides do not serve as primers, probes or templates during the amplification reaction. In one embodiment, each one oligonucleotide from the one or more oligonucleotides has a melting temperature that is at least 5° C. lower than an extension temperature used during the amplification reaction. In another embodiment, each one oligonucleotide from the one or more oligonucleotides has a melting temperature that is at least 5° C. lower than melting temperatures of primers and probes used during the amplification reaction. In one embodiment, each one oligonucleotide from the one or more oligonucleotides is present at a concentration that is at least fifty-fold lower than the concentration of primers and probes used during the amplification reaction. In another embodiment, each one oligonucleotide from the one or more oligonucleotide is present at a concentration that is between 0.1 nM and 2.0 nM. In one embodiment, the one or more oligonucleotides hybridize to more than 60%, more than 75%, or more than 90% of the segment of the single-stranded RNA control sequence. In one embodiment, the one or more oligonucleotides hybridize to the entire segment of the single-stranded RNA control sequence. In one embodiment, each one oligonucleotide from the one or more oligonucleotides is between 11 nucleotides and 50 nucleotides or between 11 nucleotides and 40 nucleotides in length or between 11 nucleotides and 30 nucleotides in length. In another embodiment, each one oligonucleotide from the one or more oligonucleotides has a melting temperature that ranges between 20° C. and 80° C., or between 30° C. and 70° C. or between 40° C. and 60° C. or between 48° C. and 58° C. In yet another embodiment, the sequence of each one oligonucleotide from the one or more oligonucleotides does not overlap with the sequence of another oligonucleotide from the one or more oligonucleotides. In another embodiment, the single-strand RNA control sequence is caged. The caging may be accomplished by means of encapsulation, encapsidation, trapping, or by the RNA template being inside a cell. In another embodiment, the one or more oligonucleotides comprise a group of oligonucleotides whose sequences are selected from group consisting of SEQ ID NOs: 1-10, 11-19, 20-27, and 28-35.

In another aspect, the invention relates to a method of preventing or reducing degradation of a segment of a single-stranded RNA molecule, the method comprising the steps of providing the single-stranded RNA molecule; and hybridizing the single-stranded RNA molecule with a plurality of oligonucleotides whose sequences are completely or partially complementary to the segment of the single-stranded RNA molecule, wherein the plurality of oligonucleotides hybridizes to more than 48% of the segment of the single-stranded RNA molecule, wherein each one oligonucleotide from the plurality oligonucleotides is between 11 nucleotides and 50 nucleotides in length. In one embodiment, the plurality of oligonucleotides hybridizes to more than 60%, more than 75%, or more than 90% of the segment of the single-stranded RNA molecule. In one embodiment, the plurality of oligonucleotides hybridizes to the entire segment of the single-stranded RNA molecule. In another embodiment, the providing and hybridizing steps are conducted in solution. In one embodiment, each one oligonucleotide from the plurality of oligonucleotides is between 11 nucleotides and 40 nucleotides in length or between 11 nucleotides and 30 nucleotides in length. In another embodiment, each one oligonucleotide from the plurality of oligonucleotides has a melting temperature that ranges between 20° C. and 80° C., or between 30° C. and 70° C., or between 40° C. and 60° C., or between 48° C. and 58° C. In yet another embodiment, the sequence of each one oligonucleotide from the plurality of oligonucleotides does not overlap with the sequence of another oligonucleotide from the plurality of oligonucleotides. In another embodiment, the single-stranded RNA molecule is caged. The caging may be accomplished by means of encapsulation, encapsidation, trapping, or by the RNA molecule being inside a cell. In another embodiment, the providing and hybridizing steps are conducted in solution. In another embodiment, the plurality of oligonucleotides comprises a group of oligonucleotides whose sequences are selected from group consisting of SEQ ID NOs: 1-10, 11-19, 20-27, and 28-35.

DETAILED DESCRIPTION OF THE INVENTION

Definitions

Figure 1:
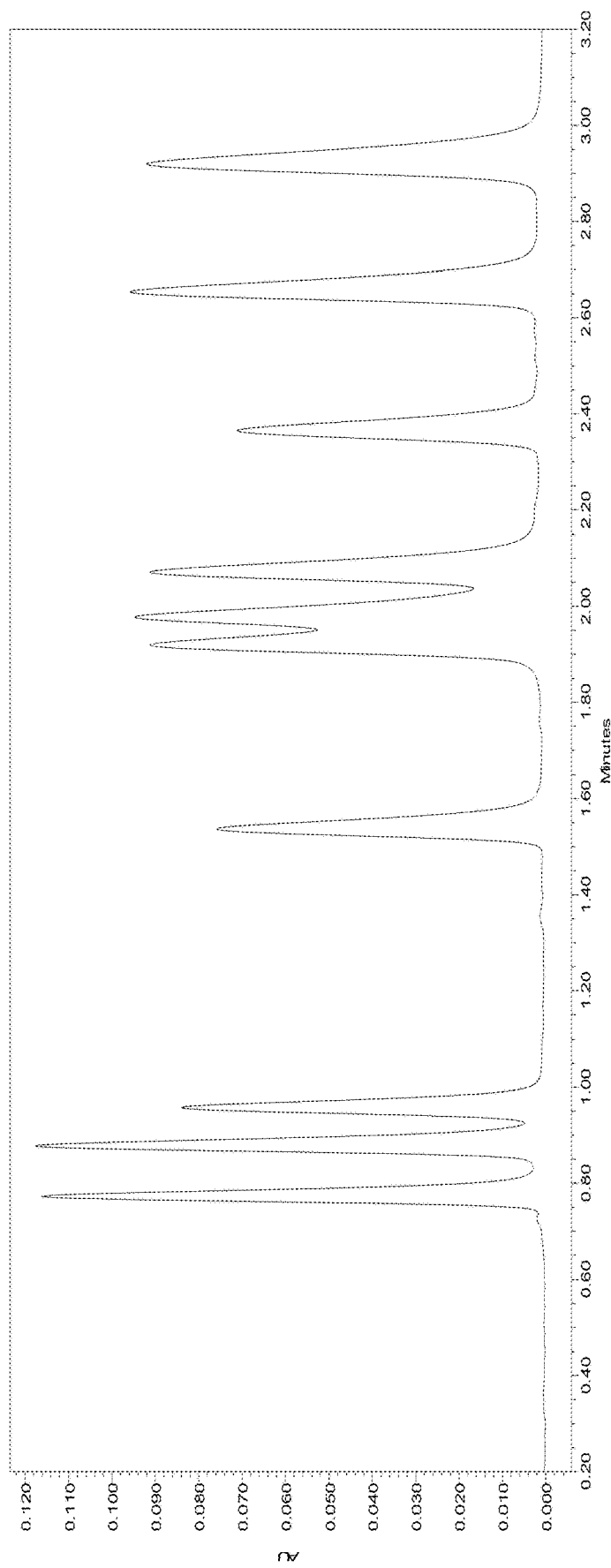
FIG. 1 shows the results of a UPLC analysis of the complementary oligonucleotide pool used in the stability experiments.

"Amplification reagents" are chemical or biochemical components that enable the amplification of nucleic acids. Such reagents comprise, but are not limited to, nucleic acid polymerases, buffers, mononucleotides such as nucleoside triphosphates, oligonucleotides e.g. as oligonucleotide primers, salts and their respective solutions, detection probes, dyes, and more.

As is known in the art, a "nucleoside" is a base-sugar combination. The base portion of the nucleoside is normally a heterocyclic base. The two most common classes of such heterocyclic bases are purines and pyrimidines.

"Nucleotides" are nucleosides that further include a phosphate group covalently linked to the sugar portion of the nucleoside. For those nucleosides that include a pentofuranosyl sugar, the phosphate group can be linked to either the 2'-, 3'- or 5'-hydroxyl moiety of the sugar. A nucleotide is the monomeric unit of an "oligonucleotide", which can be more generally denoted as an "oligomeric compound", or a "polynucleotide", more generally denoted as a "polymeric compound". Another general expression for the aforementioned is deoxyribonucleic acid (DNA) and ribonucleic acid (RNA).

An "oligomeric compound" is a compound consisting of "monomeric units" which may be nucleotides alone or non-natural compounds (see below), more specifically modified nucleotides (or nucleotide analogs) or non-nucleotide compounds, alone or combinations thereof.

"Oligonucleotides" and "modified oligonucleotides" (or "oligonucleotide analogs") are subgroups of oligomeric compounds. The term "oligonucleotide" refers to components formed from a plurality of nucleotides as their monomeric units. The phosphate groups are commonly referred to as forming the internucleoside backbone of the oligonucleotide. The normal linkage or backbone of RNA and DNA is a 3' to 5' phosphodiester linkage. Oligonucleotides and modified oligonucleotides (see below) useful for the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang S. A. et al., Methods in Enzymology 68 (1979) 90-98, the phosphodiester method disclosed by Brown E. L., et al., Methods in Enzymology 68 (1979) 109-151, the phosphoramidite method disclosed in Beaucage et al., Tetrahedron Letters 22 (1981) 1859, the H-phosphonate method disclosed in Garegg et al., Chem. Scr. 25 (1985) 280-282 and the solid support method disclosed in U.S. Pat. No. 4,458,066.

In the process described above, the oligonucleotides may be chemically modified, i.e. the primer and/or the probe comprise a modified nucleotide or a non-nucleotide compound. The probe or the primer is then a modified oligonucleotide.

"Modified nucleotides" (or "nucleotide analogs") differ from a natural nucleotide by some modification but still consist of a base, a pentofuranosyl sugar, a phosphate portion, base-like, pentofuranosyl sugar-like and phosphate-like portion or combinations thereof. For example, a label may be attached to the base portion of a nucleotide whereby a modified nucleotide is obtained. A natural base in a nucleotide may also be replaced by e.g. a 7-deazapurine whereby a modified nucleotide is obtained as well.

A "modified oligonucleotide" (or "oligonucleotide analog"), belonging to another specific subgroup of oligomeric compounds, possesses one or more nucleotides and one or more modified nucleotides as monomeric units. Thus, the term "modified oligonucleotide" (or "oligonucleotide analog") refers to structures that function in a manner substantially similar to oligonucleotides and can be used interchangeably in the context of the present invention. From a synthetical point of view, a modified oligonucleotide (or an oligonucleotide analog) can for example be made by chemical modification of oligonucleotides by appropriate modification of the phosphate backbone, ribose unit or the nucleotide bases (Uhlmann and Peyman, Chemical Reviews 90 (1990) 543; Verma S., and Eckstein F., Annu. Rev. Biochem. 67 (1998) 99-134). Representative modifications include phosphorothioate, phosphorodithioate, methyl phosphonate, phosphotriester or phosphoramidate inter-nucleoside linkages in place of phosphodiester internucleoside linkages; deaza- or azapurines and -pyrimidines in place of natural purine and pyrimidine bases, pyrimidine bases having substituent groups at the 5 or 6 position; purine bases having altered substituent groups at the 2, 6 or 8 positions or 7 position as 7-deazapurines; bases carrying alkyl-, alkenyl-, alkinyl or aryl-moieties, e.g. lower alkyl groups such as methyl, ethyl, propyl, butyl, tert-butyl, pentyl, hexyl, heptyl, octyl, nonyl, decyl, or aryl groups like phenyl, benzyl, naphtyl; sugars having substituent groups at, for example, their 2' position; or carbocyclic or acyclic sugar analogs. Other modifications are known to those skilled in the art. Such modified oligonucleotides (or oligonucleotide analogs) are best described as being functionally interchangeable with, yet structurally different from, natural oligonucleotides. In more detail, exemplary modifications are disclosed in Verma S., and Eckstein F., Annu. Rev. Biochem. 67 (1998) 99-134 or WO 02/12263. In addition, modification can be made wherein nucleoside units are joined via groups that substitute for the internucleoside phosphate or sugar phosphate linkages. Such linkages include those disclosed in Verma S., and Eckstein F., Annu. Rev. Biochem. 67 (1998) 99-134. When other than phosphate linkages are utilized to link the nucleoside units, such structures have also been described as "oligonucleosides".

A "nucleic acid" as well as the "target nucleic acid" is a polymeric compound of nucleotides as known to the expert skilled in the art. "Target nucleic acid" is used herein to denote a nucleic acid in a sample which should be analyzed, i.e. the presence, non-presence and/or amount thereof in a sample should be determined.

The term "primer" is used herein as known to the expert skilled in the art and refers to oligomeric compounds, primarily to oligonucleotides, but also to modified oligonucleotides that are able to prime DNA synthesis by a template-dependent DNA polymerase, i.e. the 3'-end of the e.g. primer provides a free 3'-OH group whereto further nucleotides may be attached by a template-dependent DNA polymerase establishing 3'- to 5'-phosphodiester linkage whereby deoxynucleoside triphosphates are used and whereby pyrophosphate is released.

A "probe" also denotes a natural or modified oligonucleotide. As known in the art, a probe serves the purpose to detect an analyte or amplificate. In the case of the process described above, probes can be used to detect the amplificates of the target nucleic acids. For this purpose, probes typically carry labels.

"Labels", often referred to as "reporter groups", are generally groups that make a nucleic acid, in particular oligonucleotides or modified oligonucleotides, as well as any nucleic acids bound thereto distinguishable from the remainder of the sample (nucleic acids having attached a label can also be termed labeled nucleic acid binding compounds, labeled probes or just probes). Exemplary labels are fluorescent labels, which are e.g. fluorescent dyes such as a fluorescein dye, a rhodamine dye, a cyanine dye, and a coumarin dye. Exemplary fluorescent dyes are FAM, HEX, JA270, CAL635, Coumarin343, Quasar705, Cyan500, CY5.5, LC-Red 640, LC-Red 705.

Any primer and/or probe may be chemically modified, i.e. the primer and/or the probe comprise a modified nucleotide or a non-nucleotide compound. The probe or the primer is then a modified oligonucleotide.

A method of nucleic acid amplification is the Polymerase Chain Reaction (PCR) which is disclosed, among other references, in U.S. Pat. Nos. 4,683,202, 4,683,195, 4,800,159, and 4,965,188. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer can be single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have e.g. been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 sec to 9 min. In order to not expose the respective polymerase like e.g. the Z05 DNA Polymerase to such high temperatures for too long and thus risking a loss of functional enzyme, it can be preferred to use short denaturation steps.

If the double-stranded template nucleic acid is denatured by heat, the reaction mixture is allowed to cool to a temperature that promotes annealing of each primer to its target sequence on the target nucleic acids.

The temperature for annealing can be from about 35° C. to about 70° C., or about 45° C. to about 65° C.; or about 50° C. to about 60° C., or about 55° C. to about 58° C. Annealing times can be from about 10 sec to about 1 min (e.g., about 20 sec to about 50 sec; about 30 sec to about 40 sec). In this context, it can be advantageous to use different annealing temperatures in order to increase the inclusivity of the respective assay. In brief, this means that at relatively low annealing temperatures, primers may also bind to targets having single mismatches, so variants of certain sequences can also be amplified. This can be desirable if e.g. a certain organism has known or unknown genetic variants which should also be detected. On the other hand, relatively high annealing temperatures bear the advantage of providing higher specificity, since towards higher temperatures the probability of primer binding to not exactly matching target sequences continuously decreases. In order to benefit from both phenomena, in some embodiments of the invention the process described above comprises annealing at different temperatures, for example first at a lower, then at a higher temperature. If, e.g., a first incubation takes place at 55° C. for about 5 cycles, non-exactly matching target sequences may be (pre-)amplified. This can be followed e.g. by about 45 cycles at 58° C., providing for higher specificity throughout the major part of the experiment. This way, potentially important genetic variants are not missed, while the specificity remains relatively high.

The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 65° C.). Extension times can be from about 10 sec to about 5 min, or about 15 sec to 2 min, or about 20 sec to about 1 min, or about 25 sec to about 35 sec. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) can be repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

PCR can be carried out in which the steps of annealing and extension are performed in the same step (one-step PCR) or, as described above, in separate steps (two-step PCR). Performing annealing and extension together and thus under the same physical and chemical conditions, with a suitable enzyme such as, for example, the Z05 DNA polymerase, bears the advantage of saving the time for an additional step in each cycle, and also abolishing the need for an additional temperature adjustment between annealing and extension. Thus, the one-step PCR reduces the overall complexity of the respective assay.

In general, shorter times for the overall amplification can be preferred, as the time-to-result is reduced and leads to a possible earlier diagnosis.

Other nucleic acid amplification methods to be used comprise the Ligase Chain Reaction (LCR; Wu D. Y. and Wallace R. B., Genomics 4 (1989) 560-69; and Barany F., Proc. Natl. Acad. Sci. USA 88 (1991) 189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Qb-amplification (for a review see e.g. Whelen A. C. and Persing D. H., Annu. Rev. Microbiol. 50(1996) 349-373; Abramson R. D. and Myers T. W., Curr Opin Biotechnol 4 (1993) 41-47).

The internal control nucleic acid used in the present invention may exhibit the following properties relating to its sequence:
  a melting temperature from 55° C. to 90° C., or from 65° C. to 85° C., or from 70° C. to 80° C., or about 75° C.
  a length of up to 500 bases or base pairs, or from 50 to 300 bases or base pairs, or from 100 to 200 bases or base pairs, or about 180 bases or base pairs
  a GC content from 30% to 70%, or from 40% to 60%, or about 50%.

A "sequence" is the primary structure of a nucleic acid, i.e. the specific arrangement of the single nucleobases of which the respective nucleic acids consists. It has to be understood that the term "sequence" does not denote a specific type of nucleic acid such as RNA or DNA, but applies to both as well as to other types of nucleic acids such as e.g. PNA or others. Where nucleobases correspond to each other, particularly in the case of uracil (present in RNA)

and thymine (present in DNA), these bases can be considered equivalent between RNA and DNA sequences, as well-known in the pertinent art.

Clinically relevant nucleic acids are often DNA which can be derived e.g. from DNA viruses like e.g. Hepatitis B Virus (HBV), Cytomegalovirus (CMV) and others, or bacteria like e.g. *Chlamydia trachomatis* (CT), *Neisseria gonorrhoeae* (NG) and others. In such cases, it can be advantageous to use an internal control nucleic acid consisting of DNA, in order to reflect the target nucleic acids properties.

On the other hand, numerous nucleic acids relevant for clinical diagnostics are ribonucleic acids, like e.g. the nucleic acids from RNA viruses such as for example Human Immunodeficiency Virus (HIV), Hepatitis C Virus (HCV), the West Nile Virus (WNV), Human Papilloma Virus (HPV), Japanese Encephalitis Virus (JEV), St. Louis Encephalitis Virus (SLEV) and others. The present invention can be readily applied to such nucleic acids. In this case, it can be advantageous to use an internal control nucleic acid consisting of RNA, in order to reflect the target nucleic acids properties. If both RNA and DNA are to be analyzed in the process described supra, the internal control nucleic acid can be RNA, as the internal control nucleic acid mimics the most sensitive target of an assay involving multiple targets, and RNA targets usually have to be more closely controlled.

Thus, an aspect of the invention is the method described above, wherein said internal control nucleic acid is RNA.

Since RNA is more prone to degradation than DNA due to influences such as alkaline pH, ribonucleases etc., internal control nucleic acids made of RNA may be provided as armored particles. Armored particles such as especially armored RNA are described e.g. in EP910643. In brief, the RNA, which can be produced chemically or heterologously e.g. by bacteria such as e.g. *E. coli*, is at least partially encapsulated in a viral coat protein. The latter confers resistance of the RNA towards external influences, in particular ribonucleases. It must be understood that internal control DNA can also be provided as an armored particle. Both armored RNA and DNA are useful as internal control nucleic acids. In an embodiment, RNA control nucleic acids are armored with the MS2 coat protein in *E. coli*. In a further embodiment, DNA control nucleic acids are armored using lambda phage GT11.

Therefore, an aspect of the invention is the method described above, wherein said internal control nucleic acid is an armored nucleic acid.

Typically, in amplification-based nucleic acid diagnostics, RNA templates are reverse transcribed into DNA prior to amplification and detection.

A "polymerase with reverse transcriptase activity" is a nucleic acid polymerase capable of synthesizing DNA based on an RNA template. It is also capable of replicating a single or double-stranded DNA once the RNA has been reverse transcribed into a single strand cDNA. In an embodiment of the invention, the polymerase with reverse transcriptase activity is thermostable.

As used herein, the term "a segment of a single-stranded RNA template" or "a segment of a single-stranded RNA control sequence" refers to the portion of an RNA template or sequence whose degradation is prevented or reduced by the one or more oligonucleotides that are used in the methods of the present invention. In some cases, the segment can cover the entire RNA template or sequence and in other cases, the segment can cover the portion of the RNA template or sequence that is amplified and detected.

In an embodiment, the process according to the invention comprises incubating a sample containing an RNA template with an oligonucleotide primer sufficiently complementary to said RNA template to hybridize with the latter, and a thermostable DNA polymerase in the presence of at least all four natural or modified deoxyribonucleoside triphosphates, in an appropriate buffer comprising a metal ion buffer which, in an embodiment, buffers both the pH and the metal ion concentration. This incubation is performed at a temperature sufficient for said primer to hybridize to said RNA template and said DNA polymerase to catalyze the polymerization of said deoxyribonucleoside triphosphates to form a cDNA sequence complementary to the sequence of said RNA template.

As used herein, the term "cDNA" refers to a complementary DNA molecule synthesized using a ribonucleic acid strand (RNA) as a template. The RNA may e.g. be mRNA, tRNA, rRNA, or another form of RNA, such as viral RNA. The cDNA may be single-stranded, double-stranded or may be hydrogen-bonded to a complementary RNA molecule as in an RNA/cDNA hybrid.

A primer suitable for annealing to an RNA template may also be suitable for amplification by PCR. For PCR, a second primer, complementary to the reverse transcribed cDNA strand, provides an initiation site for the synthesis of an extension product.

In the amplification of an RNA molecule by a DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "homogeneous", in this context, refers to a two-step single addition reaction for reverse transcription and amplification of an RNA target. By homogeneous it is meant that following the reverse transcription (RT) step, there is no need to open the reaction vessel or otherwise adjust reaction components prior to the amplification step. In a non-homogeneous RT/PCR reaction, following reverse transcription and prior to amplification one or more of the reaction components such as the amplification reagents are e.g. adjusted, added, or diluted, for which the reaction vessel has to be opened, or at least its contents have to be manipulated. Both homogeneous and non-homogeneous embodiments are comprised by the scope of the invention.

Reverse transcription is an important step in an RT/PCR. It is, for example, known in the art that RNA templates show a tendency towards the formation of secondary structures that may hamper primer binding and/or elongation of the cDNA strand by the respective reverse transcriptase. Thus, relatively high temperatures for an RT reaction are advantageous with respect to efficiency of the transcription. On the other hand, raising the incubation temperature also implies higher specificity, i.e. the RT primers will not anneal to sequences that exhibit mismatches to the expected sequence or sequences. Particularly in the case of multiple different target RNAs, it can be desirable to also transcribe and subsequently amplify and detect sequences with single mismatches, e.g. in the case of the possible presence of unknown or rare substrains or subspecies of organisms in the fluid sample.

In order to benefit from both advantages described above, i.e. the reduction of secondary structures and the reverse transcription of templates with mismatches, the RT incubation can be carried out at more than one different temperature.

Therefore, an aspect of the invention is the process described above, wherein said incubation of the polymerase with reverse transcriptase activity is carried out at different temperatures from 30° C. to 75° C., or from 45° C. to 70° C., or from 55° C. to 65° C.

As a further important aspect of reverse transcription, long RT steps can damage the DNA templates that may be present in the fluid sample. If the fluid sample contains both RNA and DNA species, it is thus favorable to keep the duration of the RT steps as short as possible, but at the same time ensuring the synthesis of sufficient amounts of cDNA for the subsequent amplification and optional detection of amplificates.

Thus, an aspect of the invention is the process described above, wherein the period of time for incubation of the polymerase with reverse transcriptase activity is up to 30 minutes, 20 minutes, 15 minutes, 12.5 minutes, 10 minutes, 5 minutes, or 1 minute.

A further aspect of the invention is the process described above, wherein the polymerase with reverse transcriptase activity and comprising a mutation is selected from the group consisting of
a) a CS5 DNA polymerase
b) a CS6 DNA polymerase
c) a *Thermotoga maritima* DNA polymerase
d) a *Thermus aquaticus* DNA polymerase
e) a *Thermus thermophilus* DNA polymerase
f) a *Thermus flavus* DNA polymerase
g) a *Thermus filiformis* DNA polymerase
h) a *Thermus* sp. sps17 DNA polymerase
i) a *Thermus* sp. Z05 DNA polymerase
j) a *Thermotoga* neapolitana DNA polymerase
k) a *Termosipho africanus* DNA polymerase
l) a *Thermus caldophilus* DNA polymerase Particularly suitable for these requirements are enzymes carrying a mutation in the polymerase domain that enhances their reverse transcription efficiency in terms of a faster extension rate.

Therefore, an aspect of the invention is the process described above, wherein the polymerase with reverse transcriptase activity is a polymerase comprising a mutation conferring an improved nucleic acid extension rate and/or an improved reverse transcriptase activity relative to the respective wildtype polymerase.

In an embodiment, in the process described above, the polymerase with reverse transcriptase activity is a polymerase comprising a mutation conferring an improved reverse transcriptase activity relative to the respective wildtype polymerase.

Polymerases carrying point mutations that render them particularly useful are disclosed in WO 2008/046612. In particular, polymerases to be used can be mutated DNA polymerases comprising at least the following motif in the polymerase domain:

T-G-R-L-S-S-Xb7-Xb8-P-N-L-Q-N; wherein Xb7 is an amino acid selected from S or T and wherein Xb8 is an amino acid selected from G, T, R, K, or L, wherein the polymerase comprises 3'-5' exonuclease activity and has an improved nucleic acid extension rate and/or an improved reverse transcription efficiency relative to the wildtype DNA polymerase, wherein in said wildtype DNA polymerase Xb8 is an amino acid selected from D, E or N.

One example is mutants of the thermostable DNA polymerase from *Thermus* species Z05 (described e.g. in U.S. Pat. No. 5,455,170), said variations comprising mutations in the polymerase domain as compared with the respective wildtype enzyme Z05. An embodiment for the method according to the invention is a mutant Z05 DNA polymerase wherein the amino acid at position 580 is selected from the group consisting of G, T, R, K and L.

For reverse transcription using a thermostable polymerase, Mn2+ can be the divalent cation and is typically included as a salt, for example, manganese chloride (MnCl2), manganese acetate (Mn(OAc)2), or manganese sulfate (MnSO4). If MnCl2 is included in a reaction containing 50 mM Tricine buffer, for example, the MnCl2 is generally present at a concentration of 0.5-7.0 mM; 2.5-3.5 mM is generally present when 200 µM of each dGTP, dATP, dUTP, and, dCTP are utilized.

Since it is in the scope of the invention to reverse-transcribe RNA target nucleic acids into cDNA while preserving the DNA target nucleic acids so both cDNA and DNA can be used for subsequent amplification, the internally controlled process described above is particularly useful for the simultaneous amplification of target nucleic acids derived from both organisms having an RNA or organisms having a DNA genome. This advantage considerably increases the spectrum of different organisms, especially pathogens, that can be analyzed under identical physical conditions.

An "organism", as used herein, means any living single- or multicellular life form. In the context of the invention, a virus is an organism.

Especially due to an appropriate temperature optimum, enzymes like Tth polymerase or, for example, the mutant Z05 DNA polymerase mentioned above are suited to carry out the subsequent step of amplification of the target nucleic acids. Exploiting the same enzyme for both reverse transcription an amplification contributes to the ease of carrying out the process and facilitates its automation, since the fluid sample does not have to be manipulated between the RT and the amplification step.

The target of the amplification step can be an RNA/DNA hybrid molecule. The target can be a single-stranded or double-stranded nucleic acid. Although the most widely used PCR procedure uses a double-stranded target, this is not a necessity. After the first amplification cycle of a single-stranded DNA target, the reaction mixture contains a double-stranded DNA molecule consisting of the single-stranded target and a newly synthesized complementary strand. Similarly, following the first amplification cycle of an RNA/cDNA target, the reaction mixture contains a double-stranded cDNA molecule. At this point, successive cycles of amplification proceed as described above.

Suitable nucleic acid detection methods are known to the expert in the field and are described in standard textbooks as Sambrook J. et al., Molecular Cloning: A Laboratory Manual, Cold Spring Harbor Laboratory Press, Cold Spring Harbor, N.Y., 1989 and Ausubel F. et al.: Current Protocols in Molecular Biology 1987, J. Wiley and Sons, NY. There may be also further purification steps before the nucleic acid detection step is carried out as e.g. a precipitation step. The detection methods may include but are not limited to the binding or intercalating of specific dyes as ethidium bromide which intercalates into the double-stranded DNA and changes its fluorescence thereafter. The purified nucleic acid may also be separated by electrophoretic methods optionally after a restriction digest and visualized thereafter. There are also probe-based assays which exploit the oligonucleotide hybridization to specific sequences and subsequent detection of the hybrid.

The amplified target nucleic acids can be detected during or after the amplification reaction in order to evaluate the result of the analysis. Particularly for detection in real time, it is advantageous to use nucleic acid probes.

It can be favorable to monitor the amplification reaction in real time, i.e. to detect the target nucleic acids and/or their amplicons during the amplification itself.

The methods set out above can be based on Fluorescence Resonance Energy Transfer (FRET) between a donor fluorescent moiety and an acceptor fluorescent moiety. A representative donor fluorescent moiety is fluorescein, and representative corresponding acceptor fluorescent moieties include LC-Red 640, LC-Red 705, Cy5, and Cy5.5. Typically, detection includes exciting the sample at a wavelength absorbed by the donor fluorescent moiety and visualizing and/or measuring the wavelength emitted by the corresponding acceptor fluorescent moiety. In the process according to the invention, detection can be followed by quantitating the FRET. For example, detection is performed after each cycling step. For example, detection is performed in real time. By using commercially available real-time PCR instrumentation (e.g., LightCycler™ or TaqMan®), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The following patent applications describe real-time PCR as used in the LightCycler™ technology: WO 97/46707, WO 97/46714 and WO 97/46712. The LightCycler™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the thermal chamber.

TaqMan® technology utilizes a single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. Typical fluorescent dyes used in this format are for example, among others, FAM, HEX, CY5, JA270, Cyan and CY5.5. During the annealing step of the PCR reaction, the labeled hybridization probe binds to the target nucleic acid (i.e., the amplification product) and is degraded by the 5' to 3' exonuclease activity of the Taq or another suitable polymerase as known by the skilled artisan, such as a mutant Z05 polymerase, during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected.

In both detection formats described above, the intensity of the emitted signal can be correlated with the number of original target nucleic acid molecules.

As an alternative to FRET, an amplification product can be detected using a double-stranded DNA binding dye such as a fluorescent DNA binding dye (e.g., SYBRGREEN I® or SYBRGOLD® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g. a hairpin). As a result of secondary structure formation within the probe, both fluorescent moieties are in spatial proximity when the probe is in solution. After hybridization to the amplification products, the secondary structure of the probe is disrupted and the fluorescent moieties become separated from one another such that after excitation with light of a suitable wavelength, the emission of the first fluorescent moiety can be detected.

Thus, in a method according to the invention is the method described above using FRET, wherein said probes comprise a nucleic acid sequence that permits secondary structure formation, wherein said secondary structure formation results in spatial proximity between said first and second fluorescent moiety.

Efficient FRET can only take place when the fluorescent moieties are in direct local proximity and when the emission spectrum of the donor fluorescent moiety overlaps with the absorption spectrum of the acceptor fluorescent moiety.

Thus, in an embodiment, said donor and acceptor fluorescent moieties are within no more than 5 nucleotides of each other on said probe.

In a further embodiment, said acceptor fluorescent moiety is a quencher.

As described above, in the TaqMan® format, during the annealing step of the PCR reaction, the labeled hybridization probe binds to the target nucleic acid (i.e., the amplification product) and is degraded by the 5'- to 3'-exonuclease activity of the Taq or another suitable polymerase as known by the skilled artisan, such as a mutant Z05 polymerase, during the subsequent elongation phase.

Thus, in an embodiment, in the process described above, amplification employs a polymerase enzyme having 5'- to 3'-exonuclease activity.

It is further advantageous to carefully select the length of the amplicon that is yielded as a result of the process described above. Generally, relatively short amplicons increase the efficiency of the amplification reaction. Thus, an aspect of the invention is the process described above, wherein the amplified fragments comprise up to 450 bases, up to 300 bases, up to 200 bases, or up to 150 bases.

The internal control nucleic acid used in the present invention can serve as a "quantitative standard nucleic acid" which is apt to be and used as a reference in order to quantify, i.e. to determine the quantity of the target nucleic acids. For this purpose, one or more quantitative standard nucleic acids undergo all possible sample preparation steps along with the target nucleic acids. Moreover, a quantitative standard nucleic acid is processed throughout the method within the same reaction mixture. It must generate, directly or indirectly, a detectable signal both in the presence or absence of the target nucleic acid. For this purpose, the concentration of the quantitative standard nucleic acid has to be carefully optimized in each test in order not to interfere with sensitivity but in order to generate a detectable signal also e.g. at very high target concentrations. In terms of the limit of detection (LOD, see below) of the respective assay, the concentration range for the "quantitative standard nucleic acid" is 20-5000×LOD, 20-1000×LOD, or 20-5000× LOD. The final concentration of the quantitative standard nucleic acid in the reaction mixture is dependent on the quantitative measuring range accomplished.

"Limit of detection" or "LOD" means the lowest detectable amount or concentration of a nucleic acid in a sample. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is copy of the respective nucleic acid. IU/ml stands for "International units/ml", referring to the WHO standard.

A widely used method for calculating an LOD is "Probit Analysis", which is a method of analyzing the relationship between a stimulus (dose) and the quantal (all or nothing) response. In a typical quantal response experiment, groups of animals are given different doses of a drug. The percent dying at each dose level is recorded. These data may then be analyzed using Probit Analysis. The Probit Model assumes that the percent response is related to the log dose as the cumulative normal distribution. That is, the log doses may be used as variables to read the percent dying from the cumulative normal. Using the normal distribution, rather than other probability distributions, influences the predicted response rate at the high and low ends of possible doses, but has little influence near the middle.

The Probit Analysis can be applied at distinct "hitrates". As known in the art, a "hitrate" is commonly expressed in percent [%] and indicates the percentage of positive results at a specific concentration of an analyte. Thus for example, an LOD can be determined at 95% hitrate, which means that the LOD is calculated for a setting in which 95% of the valid results are positive.

In an embodiment, the process described above provides an LOD of 1 to 100 cp/ml or 0.5 to 50 IU/ml, or 1 to 75 cp/ml or 0.5 to 30 IU/ml, or 1 to 25 cp/ml or 1 to 20 IU/ml.

With respect to some examples of possible target nucleic acids from certain viruses, the process described above provides the following LODs:

HIV: up to 60 cp/ml, up to 50 cp/ml, up to 40 cp/ml, up to 30 cp/ml, up to 20 cp/ml, or up to 15 cp/ml
HBV: up to 10 IU/ml, up to 7.5 IU/ml, or up to 5 IU/ml
HCV: up to 10 IU/ml, up to 7.5 IU/ml, or up to 5 IU/ml
WNV I: up to 20 cp/ml, up to 15 cp/ml, or up to 10 cp/ml
WNV II: up to 20 cp/ml, up to 15 cp/ml, up to 10 cp/ml, or up to 5 cp/ml
JEV: up to 100 cp/ml, up to 75 cp/ml, up to 50 cp/ml, or up to 30 cp/ml
SLEV: up to 100 cp/ml, up to 75 cp/ml, up to 50 cp/ml, up to 25 cp/ml, or up to 10 cp/ml.

An example of how to perform calculation of quantitative results in the TaqMan® format based on an internal control nucleic acid serving as a quantitative standard nucleic acid is described in the following: A titer is calculated from input data of instrument-corrected fluorescence values from an entire PCR run. A set of samples containing a target nucleic acid and an internal control nucleic acid serving as a quantitative standard nucleic acid undergo PCR on a thermocycler using a specified temperature profile. At selected temperatures and times during the PCR profile samples are illuminated by filtered light and the filtered fluorescence data are collected for each sample for the target nucleic acid and the internal control nucleic acid. After a PCR run is complete, the fluorescence readings are processed to yield one set of dye concentration data for the internal control nucleic acid and one set of dye concentration data for the target nucleic acid. Each set of dye concentration data is processed in the same manner. After several plausibility checks, the elbow values (CT) are calculated for the internal control nucleic acid and the target nucleic acid. The elbow value is defined as the point where the fluorescence of the target nucleic acid or the internal control nucleic acid crosses a predefined threshold (fluorescence concentration). Titer determination is based on the assumptions that the target nucleic acid and the internal control nucleic acid are amplified with the same efficiency and that at the calculated elbow value equal amounts of amplicon copies of target nucleic acid and internal control nucleic acid are amplified and detected. Therefore, the (CTQS−CTtarget) is linear to log (target conc/QS conc). In this context, QS denotes the internal control nucleic acid serving as a quantitative standard nucleic acid. The titer T can then be calculated for instance by using a polynomial calibration formula as in the following equation:

$$T'=10(a(CTQS-CTtarget)2+b(CTQS-CTtarget)+c)$$

The polynomial constants and the concentration of the quantitative standard nucleic acid are known, therefore the only variable in the equation is the difference (CTQS−CTtarget).

Further, the internal control nucleic acid can serve as a "qualitative internal control nucleic acid". A "qualitative internal control nucleic acid" is particularly useful for confirming the validity of the test result of a qualitative detection assay: Even in the case of a negative result, the qualitative internal control must be detected, otherwise the test itself is considered to be inoperative. However, in a qualitative setup, it does not necessarily have to be detected in case of a positive result. As a consequence, its concentration must be relatively low. It has to be carefully adapted to the respective assay and its sensitivity. For example, the concentration range for the qualitative internal nucleic acid, i.e. the second control nucleic acid, will comprise a range of 1 copy per reaction to 1000 copies per reaction. In relation to the respective assay's limit of detection (LOD), its concentration is between the LOD of an assay and the 25 fold value of the LOD, or between the LOD and 10×LOD. Or, it is between 2× and 10×LOD. Or, it is between 5× and 10×LOD. Or, it is 5× or 10×LOD.

A primary aspect of the invention is the preparation and use of nuclease and hydrolysis resistant nucleic acid standards and controls. Internal standards and positive controls play an important role in assuring the correct functioning of the test kits, and confirming test results. Internal standards also provide a means for quantification. The detection and quantification of specific RNAs in samples has become prevalent with the advent of RT-PCR. The internal standard for RT-PCR studies should be an RNA molecule, as it controls for both the reverse transcription and PCR amplification steps. This is problematic, as RNA is particularly susceptible to RNase and thermal degradation. Altered test results could be produced by partial or complete degradation of an RNA standard either during storage or after introduction to a sample. The likelihood of at least partial RNA degradation is quite high, given that many of the RNA detection schemes are designed to detect viral RNAs in serum samples, where relatively high quantities of various RNases are located. The ideal internal standard for RNA diagnostic assays is a molecule that is functionally equivalent to RNA in the assay format, but resistant to degradation by nucleases or by hydrolysis. Three general methods can be imagined for protecting RNA from enzyme-mediated degradation in an environment in which RNases are active: (1) microencapsulating the RNA inside an impenetrable structure, (2) non-covalently binding the RNA with molecules that deny access of nucleases to the standard, and (3) chemically altering the structure of the RNA in such a way that it is no longer a substrate for nucleases while still being functionally equivalent to RNA in the assay format.

The nucleic acids in the standards of the invention can be used in quantifying assays. These standards may be used for a variety of purposes such as quantitative RNA standards (to determine the absolute copy number of a specific RNA sequence), specifically to quantify the number of RNA viruses such as HIV-1, HIV-2, HCV, HTLV-1, HTLV-2, hepatitis G, enterovirus, dengue fever virus, or rabies, in plasma, serum, or spinal fluid. They may also be used to quantify the expression of specific mRNA in cells or tissue by an RT-PCR assay. The standards may be internal or external. An internal standard is mixed with the sample at a known concentration such that the sample and the standard are processed and assayed as one. Thus, differences in the efficiency of the assay from sample to sample are normalized using the signal generated by the internal standard. An external standard is processed and assayed at a known concentration in parallel with the sample but it is processed separately from the sample. Several different concentrations of the external standard may be processed simultaneously to produce a standard curve which may then be used to determine the value of the unknown sample. Internal and external standards may both be used for quantification but internal standards are generally regarded as more accurate. The standards may be used as qualitative standards acting as positive controls in diagnostics, for example, bacterial, fungal, or parasitic diseases which are diagnostics RNA based or in RT-PCR assays to indicate that all of the reagents are functioning properly. These standards may be used to measure the integrity of an RNA isolation procedure by measuring the amount of degradation observed in the protected RNA after it has been subjected to the isolation procedure followed by Northern blotting. They may be used as environmental tracers to follow the flow of groundwater or to label the waste of individual companies with a unique nucleic acid sequence which can be traced back to the offending company.

The present invention is particularly useful for viral quantification. There are many new nucleic acid based assays in the process of being developed and/or marketed. These assays detect pathogenic human viruses such as HIV and HCV in human plasma or serum. These assays are highly sensitive, detecting even less than 300 virions per 1.0 ml of plasma. In their current format, several of these nucleic acid based assays use naked RNA for their quantitative standards. Unfortunately, these naked RNA standards are very susceptible to contaminating ribonuclease and thermally mediated hydrolysis and thus the results of the assay may be compromised.

One primary embodiment of the present invention relates to nucleic acid standards comprising nuclease and hydrolysis resistant recombinant nucleic acid segments comprising a sequence coding a standard nucleic acid. In some preferred embodiments, the nucleic acid standard is an RNA standard comprising a ribonuclease and hydrolysis resistant RNA segment comprising a sequence coding a standard RNA. As used herein the terms "standard nucleic acid" and "standard RNA" refer respectively to nucleic acids and RNAs that are suitable for use as a standard in the particular assay to be employed. The present invention contemplates a ribonuclease and hydrolysis resistant recombinant RNA which is highly suitable as an RNA standard for quantifying RNA viruses, although it need not be recombinant and may be used as an RNA standard for RNA isolated from any source, such as cells from tissue cultures.

The terms "nuclease resistant" and "ribonuclease resistant" mean that a nucleic acid exhibits some degree of increased resistance to nuclease over a naked, unmodified nucleic acid of the same sequence. Similarly, the term "hydrolysis resistant" means that a nucleic acid exhibits some degree of increased resistance to spontaneous temperature dependent hydrolysis over a naked, unmodified nucleic acid of the same sequence.

There are a variety of methods that may be employed to render a nucleic acid segment nuclease resistant. The nucleic acid segment may be chemically modified, coated with a nuclease resistant coating, or caged in a nuclease resistant structure. For example, the RNA standard can be a chemically modified RNA that is resistant to ribonuclease. Another way in which to render a recombinant RNA segment ribonuclease resistant is to coat it with a ribonuclease resistant coating. Such a coating can be anything that binds in a sequence dependent or independent manner to the RNA and renders the RNA ribonuclease resistant. In some cases, the RNA standard is a recombinant RNA that is caged from the external environment in a ribonuclease resistant structure. RNA may be caged simply by being inside a cell. Other synthetic methods of caging RNA involve the partial encapsidation of the RNA in viral proteins, partial lipid encapsulation of the RNA, partially trapping the RNA in polymer matrices, etc.

In another method, the ribonuclease or hydrolysis resistant structure is comprised of a viral coat protein that partially encapsidates the RNA standard. The RNA is transcribed in vivo in a bacterial host and then encapsidated by bacteriophage proteins. This "caging" of the RNA results in RNA which is protected from ribonuclease (Armored RNA) Although the nucleic acid or RNA may be completely or substantially caged in the nuclease resistant or hydrolysis resistant structure, partially caged nucleic acids and RNAs are also within the scope of the present invention as long as the partial caging renders the nucleic acid or RNA nuclease or ribonuclease or hydrolysis resistant. Thus, when used herein the terms "encapsidation," "encapsulation," "trapped," etc. encompass structures wherein the encapsidation, encapsulation, trapping etc. is partial as well as substantial or substantially complete so long as the resultant structure is nuclease or hydrolysis resistant as those terms are used herein.

The RNA can also be chemically modified so that it is resistant to ribonuclease. A chemically modified RNA may be comprised of chemically modified nucleotides. These nucleotides are modified so that ribonucleases cannot act on the RNA. The chemically modified RNA is prepared by chemical modification of an RNA or a previously transcribed RNA transcript. Alternatively, the chemically modified RNA may be transcribed or synthesized from nucleotides that have already been chemically modified.

An RNA standard may also comprise an RNA that is bound non-covalently, or coated with, a ribonuclease resistant coating. Such binding, which may be sequence dependent or independent, renders the RNA ribonuclease resistant.

In some embodiments, the bound molecule is comprised of a protein. Examples of such binding proteins are MS2/R17 coat protein, HIV-1 nucleocapsid protein, gp32, the regA protein of T4, or the gp32 of bacteriophage T4. In other cases, the non-covalently bound molecule is comprised of a small molecule. For example the polyamines, spermine and/or spermidine. The ribonuclease-resistant coating may also be comprised of a nucleic acid. In some preferred embodiments, the nucleic acid hybridizes to the recombinant RNA, blocks nucleases, and can serve as a primer for reverse transcriptase. In other cases, poly-L-lysine and cationic detergents such as CTAB may be used to coat and protect RNA.

A generic Internal Control/Quantitation Standard (IC/QS) concept is based on using a single control sequence (e.g. one DNA and one RNA derived from one sequence) to be used in all diagnostic assays. Historically, competitive amplification has been utilized for the design of internal controls, controls which compete with the target for the primers. Using the competitive amplification concept, each assay used individual control sequences composed of primer-binding sequences identical to the assay target and a generic probe binding site. For each new assay, the target primers served also as the control primers, thus no extra primers were needed in the assay. In multiplex assays, only one Internal Control was constructed with primer binding sites corresponding to one of the targets. The use of one IC in a multiplex assay was obviously no longer competitive for the other targets in the assay. Thus the goal of a full process control was only partly met. A second example of a non-competitive control uses an endogenous Human Genomic Internal Control derived from cells in the sample which requires its own set of primers. Key requirements of the Generic IC/QS included the following: It must meet all Regulatory needs. It should serve as a Full Process Control (FPC), an Internal Control (IC), and an Internal Quantitation Standard (IQS) in respective assays. For a FPC, it should go through sample preparation with similar efficiency to the target(s). It should not share primer and probe binding sites with any intended target, but should amplify/detect with similar efficiency, i.e. it should fail when target does and should respond to PCR inhibitors in a similar manner to the target. The Generic IC/QS should result in improved dynamic range, LOD, and assay precision and should result in reduced development time and operational complexity.

The generic control concept would consist of a common control sequence which can be either RNA or DNA, and will be protected (e.g. as in particles termed Armored RNA (MS2 phage Coat protein particles) or Armored DNA (lambda phage particles)). The generic control will have one set of new generic primers and probe to be used in all assays, if possible. To this end, a generic internal control (GIC) along with primers and probe can be designed using the NCBI Blast program and EMBOSS shuffleseq (European Molecular Biology Open Software Suite) to generate a unique sequence. The basic concept of the present invention is the concept of protecting against hydrolysis or RNase degradation of RNA by converting the specific RNA sequence of interest into a nucleic acid duplex. In one embodiment, this duplex is an RNA/DNA hybrid duplex. The rate of hydrolysis of a phosphodiester bond in duplex DNA is known to be 10-fold slower than single-stranded DNA. Also, all the common contaminating ribonucleases prefer single stranded RNA substrates. Although an RNA/DNA hybrid duplex is the preferred substrate for RNase H, this ribonuclease is not a common contaminant.

It is well known that single stranded RNA is readily hydrolyzed, and has low thermal stability. This is due to the close proximity of the 2'-hydroxyl, which can result in anchimeric assistance and transesterification followed by the ultimate strand cleavage. It is also known that the transition state leading to the 2',3'-cyclic intermediate has strict geometric and steric requirements. The 2'-hydroxyl must be able to orient itself in the correct position such that it is in line with the leaving group, leading to a transient trigonal bipyramid structure. The formation of the 2'-3'-cyclic phosphate intermediate is unrestricted in single stranded-RNA conformation, since the formation of the transition state has low energy requirements due to the flexible nature of the bonds, and the large number of degrees of freedom available. By forcing the RNA to be in a duplex form, the nucleophile and the leaving group will be constrained, and the degrees of freedom of the functional groups will be greatly reduced. With the addition of the Complementary Oligonucleotide Pools for Stabilization (COPS) of the present invention, hybridization occurs, and a DNA:RNA hybrid duplex is formed. When held in a duplex structure, RNA is rigid, and no longer flexible. In the duplex state, the 2'-hydroxyl and the phosphodiester linkage (leaving group) are not located in an opposite orientation to each other. Formation of the transition state is not possible without unwinding and breaking many hydrogen bonds. This is energetically very disfavorable, and therefore disallowed. In addition, a rigid bicyclic 2',3'-phosphate intermediate cannot be formed in an already rigid structure. This explains the extraordinary thermal stability conferred to RNA by the COPS strategy.

Thus the key features of this invention can be implemented by introducing one or more reverse complement oligonucleotide sequences to a storage solution, a specimen, or to an extraction buffer as appropriate. The entire RNA sequence to be protected may be optionally covered by hybridization to the one or more reverse complement oligonucleotide sequences. The complementary oligonucleotide sequences need not be completely complementary to the RNA sequence of interest and may be partially complementary to the RNA sequence as long as hybridization between the oligonucleotide(s) and the RNA can still occur at moderately stringent conditions, as understood in the art. The complementary oligonucleotide sequences may optionally be selected to be adjacent to each other. The concentrations, lengths, and compositions of the complementary oligonucleotide sequences are to be chosen in such a way that the downstream process steps (e.g. PCR amplification) will be minimally impacted or harmed. For example, by keeping the lengths of the oligonucleotide complements in a range (e.g. between 11 and 50 nucleotides or between 11 and 30 nucleotides in length) that allows hybridization to the RNA sequence at temperatures of 45° C. or above but minimizes binding to a solid phase in a downstream sample preparation process, any harmful interference in a subsequent RT-PCR reaction will be minimized. Additionally, by designing the oligonucleotide complements to have sufficient lower melting temperatures than the primers, and maintaining a high-enough annealing temperature during the reverse transcription (RT) step, competition with primers can be minimized. Similarly, by blocking the 3'-terminal ends of the oligonucleotide complements, any such complements that may still be present in a subsequent RT-PCR reaction will be unable to be extended by the polymerase. The concentrations of the oligonucleotide complements can also be chosen such that they are in sufficient molar excess to provide adequate protection for the RNA sequence, but are in concentration that are low enough as to not cause any harm to the downstream processes (e.g. PCR amplification).

The compositions of the complement oligonucleotide sequences are only restricted by their ability to form stable duplexes with the RNA sequences of interest. These oligonucleotides can therefore comprise of DNA, L-DNA, RNA, LNA, PNA, BNA etc., or any other known variations and modifications on the nucleotide bases, sugars, or phosphodiester backbones.

While the foregoing invention has been described in some detail for purposes of clarity and understanding, it will be clear to one skilled in the art from a reading of this disclosure that various changes in form and detail can be made without departing from the true scope of the invention. For example, all the compositions and methods described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The following examples are given to illustrate embodiments of the present invention as it is presently preferred to practice. It will be understood that the examples are illustrative, and that the invention is not be considered as restricted except as indicated in the appended claims.

EXAMPLES

The following examples illustrate the methods of the present inventions.

Example 1

DESIGN and Preparation of the Complementary Oligonucleotide Pools

Complementary oligonucleotides were designed against the RNA sequence using in silico design tools. A total of ten oligonucleotides were designed to cover the sequence of interest, varying in length between 14 and 26 bases and with a calculated Tm range of 49.9-57.9 C. These sequences were further modified with a phosphate moiety at the 3'-end. The sequences and melting temperatures of the ten oligonucleotides are shown in Table 1.

TABLE 1

| SEQ ID NO: | SEQUENCE | Tm |
|---|---|---|
| 1 | TCACCTCGCCCCGA | 53.8 |
| 2 | GAGTTCGTCGGGCCGC | 57.9 |
| 3 | GGTTGTGACCGGAACC | 51.0 |
| 4 | TGCGCGTCCCGTTTTGA | 54.7 |
| 5 | TTTTCTAGCGTTCGCCCA | 50.8 |
| 6 | AGGGGCTTTTTACGTGGGAG | 53.8 |
| 7 | TACTTCGTAACGGTGCGGGT | 54.1 |
| 8 | CTCACTTAATTGCTGGCGTCAG | 53.4 |
| 9 | CTTCATTCTTGACATGTATGGCGC | 49.9 |
| 10 | TTATACAGTACCAATCGTCGGTTCG | 55.3 |

The oligonucleotides were synthesized and purified by HPLC, and adjusted to a final concentration of 100 micromolar each. Equal volumes of these solutions were combined to provide a 10 micromolar complementary oligonucleotide pool, which was further characterized by UPLC analysis using a C18 reverse phase column and a linear gradient of triethylammonium acetate and acetonitrile. The results are shown in FIG. 1, and confirm the presence of all 10 oligonucleotides.

Example 2

Preparation of RNA and Armored RNA Samples for Accelerated Stability Studies

RNA transcript and armored RNA samples were prepared at a concentration of 300 copies per microliter in Tris.HCl (pH 7.0) containing 100 mM KCl. The complement pools, referred as Complementary Oligonucleotide Pools for Stabilization (COPS) were added to the sample at a final concentration of 0, 0.1, 1, or 10 nM. The samples were incubated at 2-8° C., 37° C. or 45° C. over a period of 18 days.

Example 3

Figure 2:
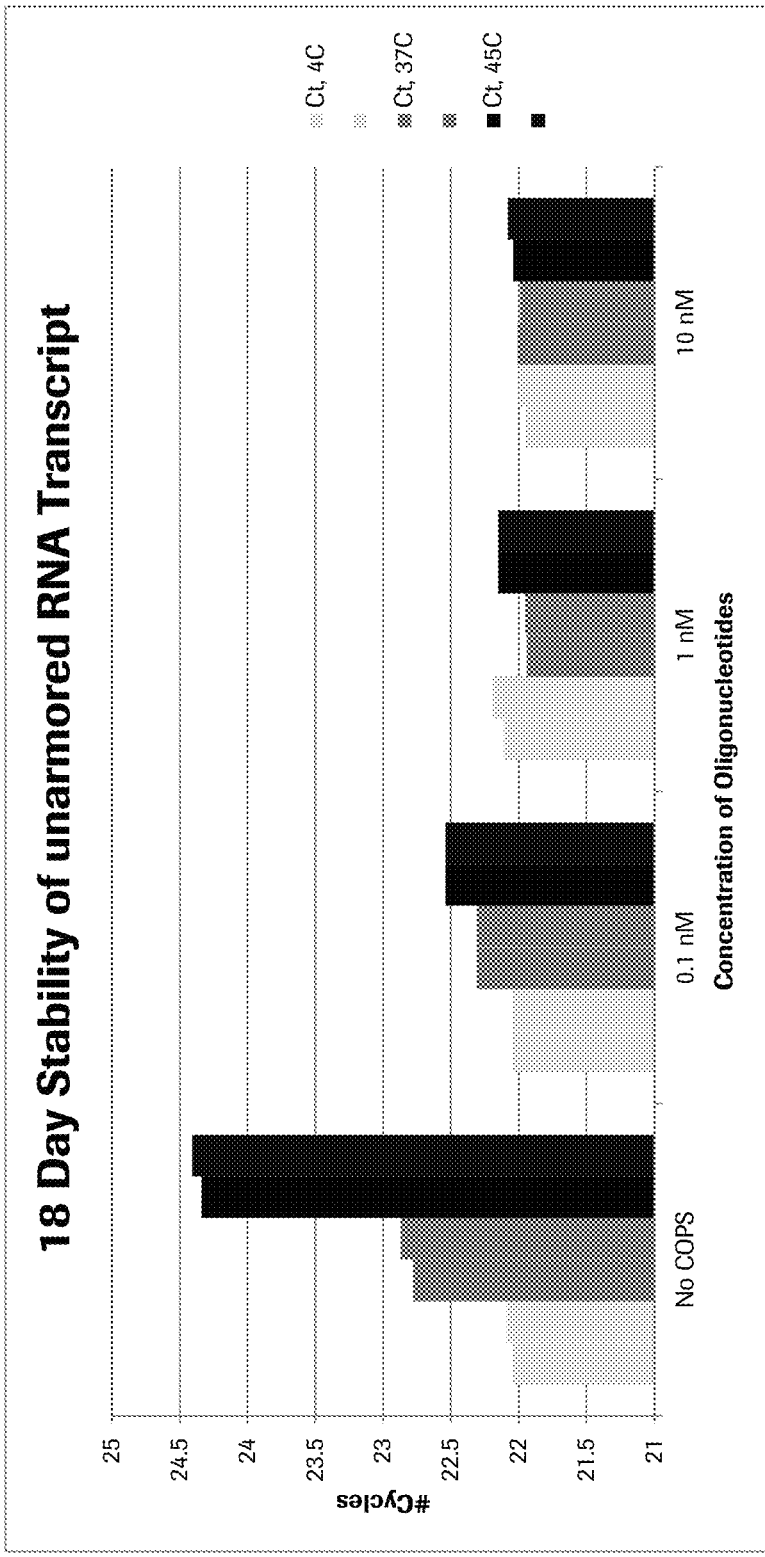
FIG. 2 shows the results of an 18-day stability study of PEF066 RNA transcript in the presence of complementary oligonucleotides. Samples were incubated at 2-8° C., 37° C., and 45° C., and amplified and detected by RT-PCR, where an increased cycle threshold (value) was indicative of sample degradation.
Figure 3:
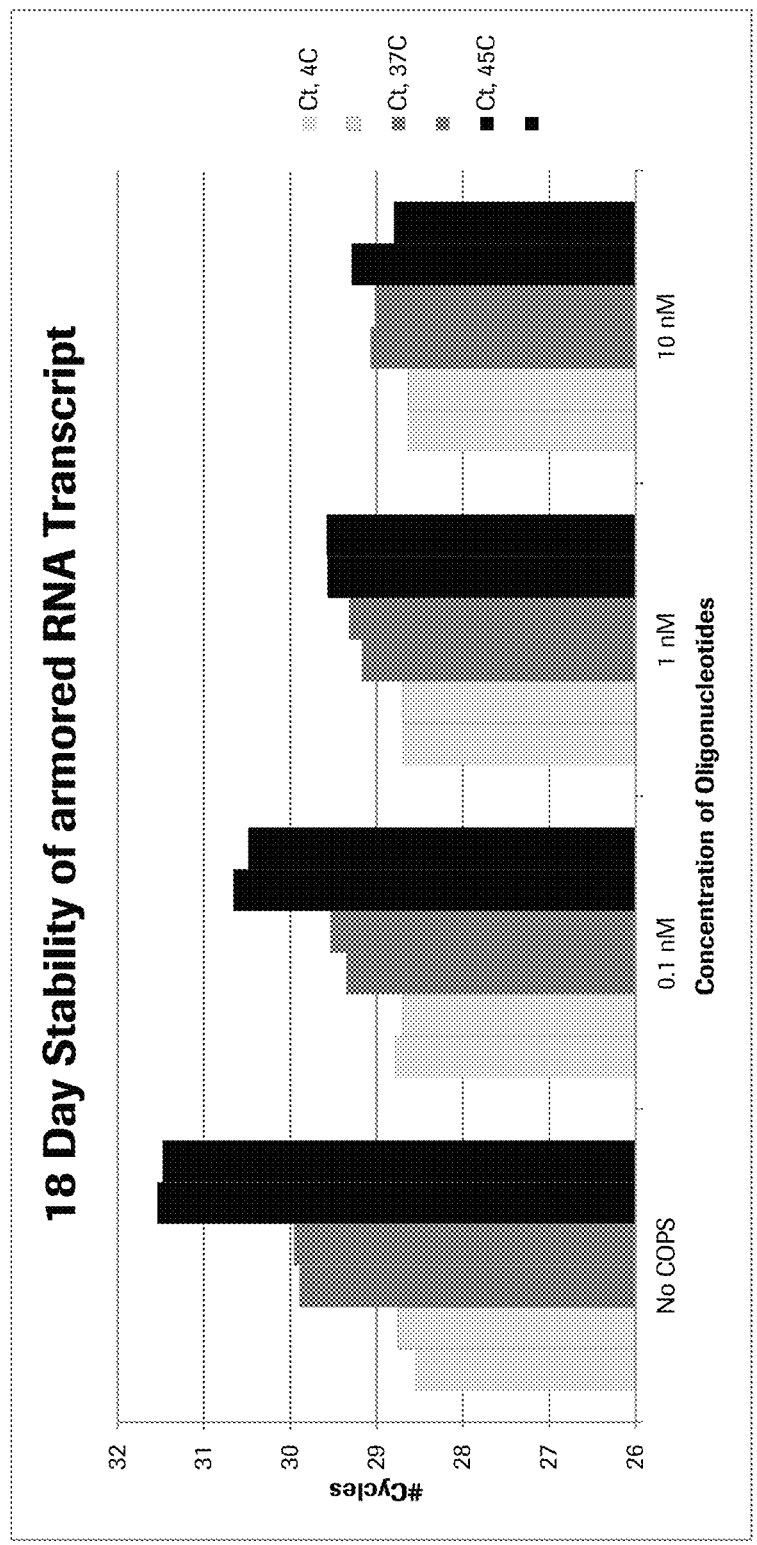
FIG. 3 shows the results of an 18-day stability study of PEF070 Armored RNA control in the presence of complementary oligonucleotides. Samples were incubated at 2-8° C., 37° C., and 45° C., and amplified and detected by RT-PCR, where an increased cycle threshold (value) was indicative of sample degradation.

Determination of RNA Stability by RT-PCR 5 microliters of each sample were amplified by Taqman® based RT-PCR. PCR reaction mixtures were prepared on a 96-well plate with the following final concentrations: 60 mM Tricine(pH 8.3), 120 mM potassium acetate, 3% glycerol, 5.4% DMSO, 0.015% Tween 20, 400 M each dATP, dCTP and dGTP, 800 M dUTP, 600 nM of each primer, 100 nM probe, target RNA transcript or armored RNA (1,500 copies), 900 units/mL ZO5D DNA polymerase (with 5' nuclease activity), 200 units/mL UNG, 44 M EDTA, and 3.3 mM manganese acetate. Reverse transcription, amplification and analysis was performed using the Roche LightCycler® 480 instrument (Roche Molecular Systems, Pleasanton, Calif.). The following temperature profile was used: 50° C. for 2 minutes, 94° C. for 5 seconds, 55° C. for 2 minutes, 60° C. for 6 minutes, 65° C. for 4 minutes, 2 cycles of 95° C. (10 seconds) to 55° C. (15 seconds) followed by cycling from 91° C. (5 seconds) to 65° C. (15 seconds) 45 times. The results of these experiments are shown in FIG. 2 and FIG. 3. As can be readily seen, in the presence of the complementary oligonucleotide pools, both the RNA transcript and armored RNA are more stable, as demonstrated by the earlier Cts compared with the samples without the COPS oligonucleotides.

Example 4

RNA Stability Study with Partial Hybridization by COPS

RNA transcript and armored RNA samples are prepared as in Example 2 with the exception that in one reaction, only COPS corresponding to SEQ ID NOs: 1, 3, 5, 7 and 10 are added (Set A) and in another reaction, only COPS corresponding to SEQ ID NOs: 2, 4, 6, 8 and 9 are added (Set B). Calculations show that Set A covers 52% of the RNA transcript/armored RNA sequence while set B covers 48% of the RNA transcript/armored RNA sequence. After 18 day incubation at 45° C., RNA stability in the absence of COPS or in the presence of Set A COPS or Set B COPS can be compared by determining the Ct values of each reaction by RT-PCR as described in Example 3.

Example 5

RNA Stability after Extended Incubation

Figure 4:
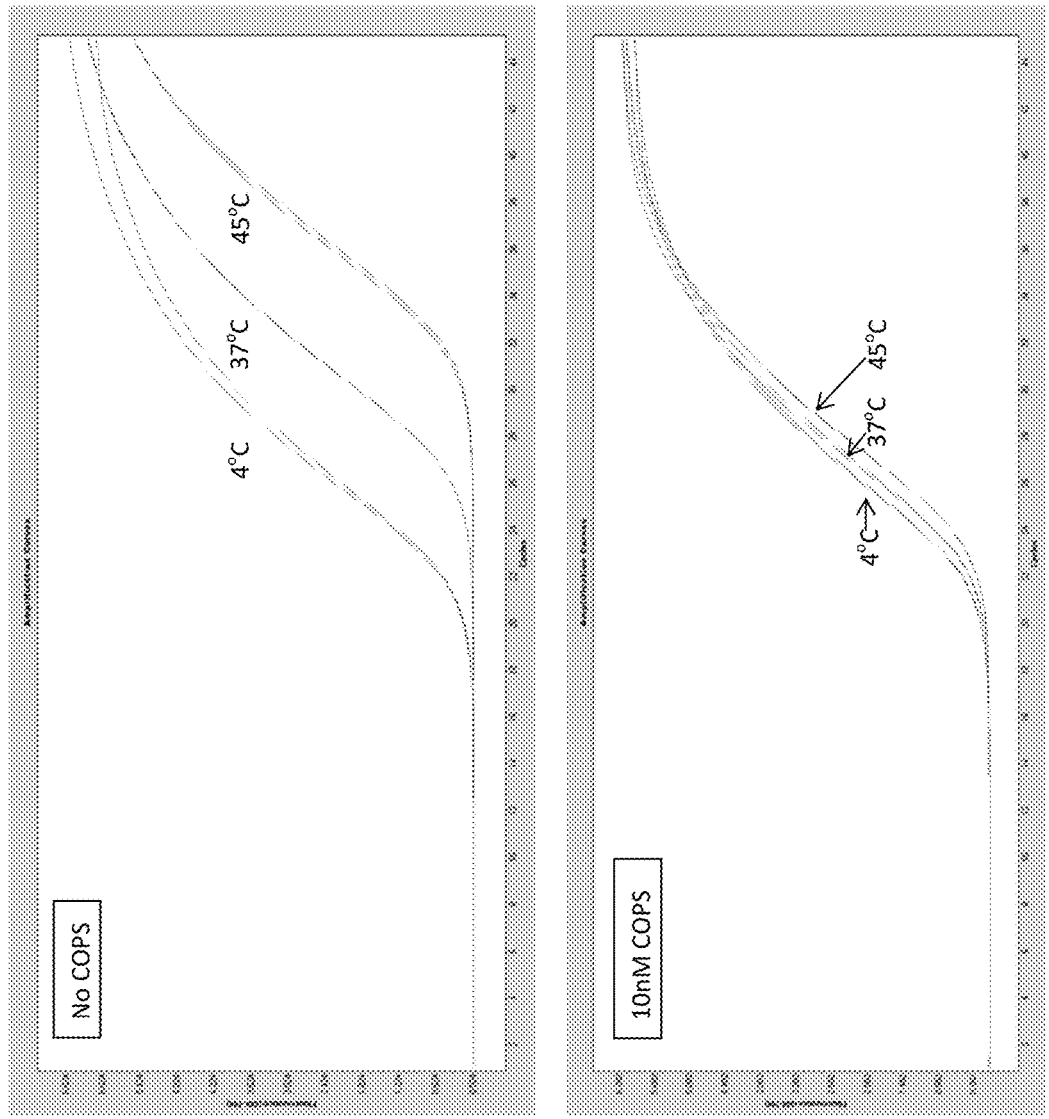
FIG. 4 shows the RT-PCR growth curves of a 12-week stability study of a PEF066 RNA transcript in the absence (TOP) or presence (BOTTOM) of complementary oligonucleotides. Samples were incubated at 4° C., 37° C., and 45° C., and amplified and detected by RT-PCR, where an increased cycle threshold (value) was indicative of sample degradation.

RNA transcript and armored RNA samples were prepared as in Example 2 except that the armored RNA was prepared at 1500 copies per microliter. COPS were then added to the samples at a final concentration of 0, 0.1, 1 or 10 nM and the samples were incubated at 4° C., 37° C. or 45° C. for 12 weeks. Determination of RNA stability by RT-PCR was performed as described in Example 3. Stability was significantly improved with the presence of COPS for both unarmored and armored RNA at 37° C. and 45° C. incubation. FIG. 4 shows the results of the RT-PCR growth curves for the unarmored RNA template. In the absence of COPS (top graph) the sample incubated at 45° C. exhibited a 10 cycle delay of the Ct value compared to the sample incubated at 4° C. In contrast, in the presence of 10 nM COPS (bottom graph), the 45° C. sample showed only a 1.4 cycle delay, demonstrating an 8.6 cycle or approximately 400-fold improvement in RNA stability. For the armored RNA experiment, a 7.4 cycle or approximately 200-fold improvement was observed (data not shown).

Example 6

Stabilization of Accuplex-Encapsulated RNA

Figure 6:
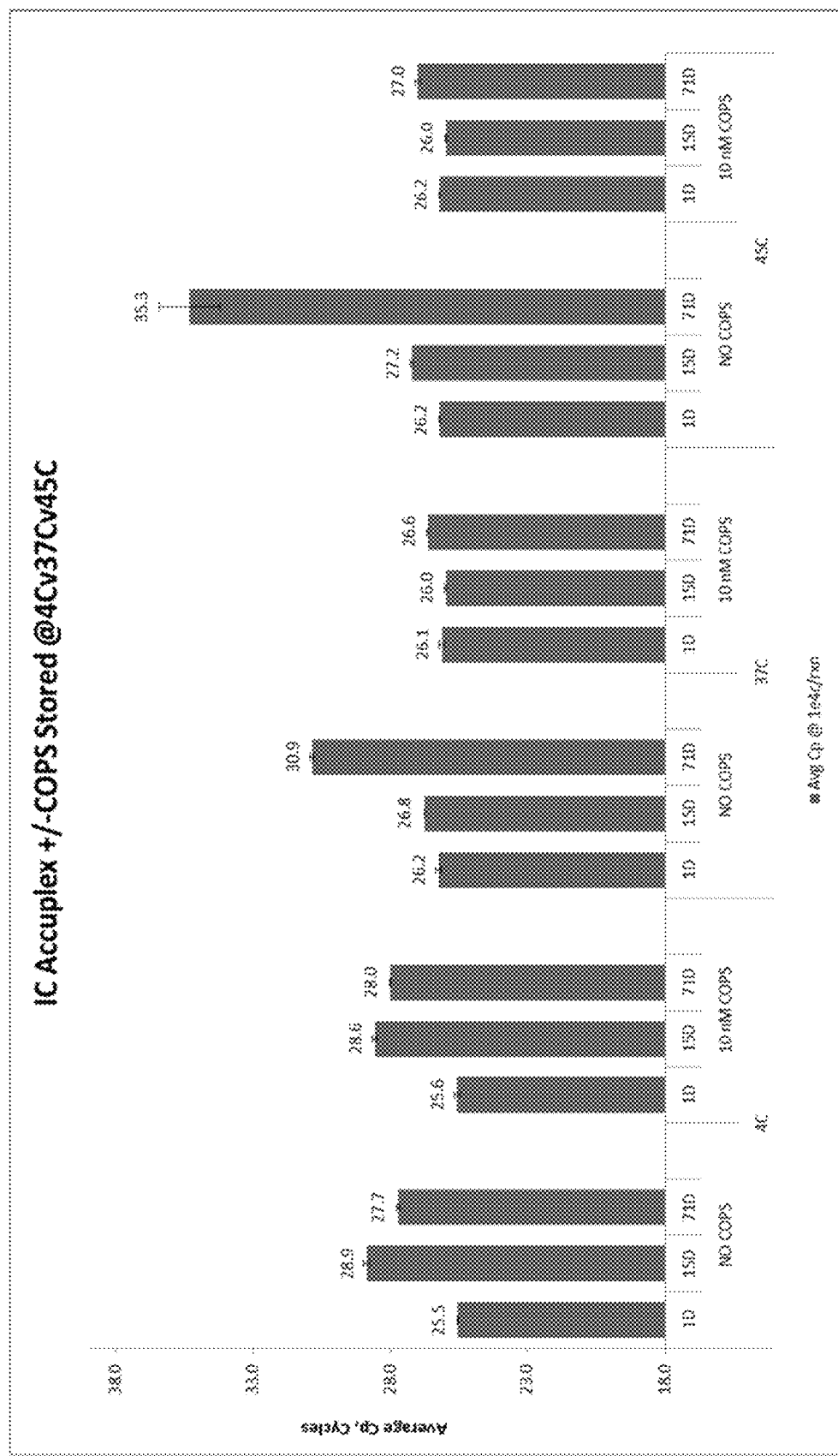
FIG. 6 shows the results of a stability study of an RNA control encapsulated in Accuplex in the absence (NO COPS) or presence (10 nM COPS) of complementary oligonucleotides. Samples incubated at either 4° C., 37° C., or 45° C. for 1 day, 15 days or 71 days were amplified and detected by RT-PCR, where increased cycle threshold (Cp value) was indicative of sample degradation.

Accuplex (SeraCare Life Sciences, Milford Mass.) is a recombinant technology capable of encapsulating an RNA molecule of interest inside a replication-deficient mammalian virus-like particle that contains both a protein coat and lipid bilayer. In order to test the utility of COPS for the stabilization of RNA inside the Accuplex particle, the RNA control sequence, pEF070, which was used to design and prepare the complementary oligonucleotides described in Example 1 was provided to SeraCare for custom preparation of Accuplex-encapsulated single-stranded RNA. COPS were then added to the Accuplex-RNA samples at 10 nM concentration and the samples were incubated at 4° C., 37° C. or 45° C. for 71 days. Determination of RNA stability by RT-PCR was performed as described in Example 3 and the results of the study are shown in FIG. 6. After 71 days of incubation, the ΔCp value between absence and presence of COPS was 4.3 (30.9-26.6) for 37° C. and 8.3 (35.3-27.0) for 45° C., clearly showing the effectiveness of COPS in reducing degradation of RNA in Accuplex particles that are stored at high temperature.

Example 7

COPS Stabilization of HIV RNA Templates

Three RNA sequences corresponding to segments of the HIV-1 GAG, HIV-1 LTR, and HIV-2 LTR regions were used as RNA templates for testing the stabilizing effects of their corresponding COPS. A total of 25 oligonucleotides, nine for HIV-GAG, eight for HIV-1 LTR and eight for HIV-2 LTR, were designed to cover the respective sequences of interest. The 25 oligonucleotides varied in length between 17 and 26 bases and their sequences are shown in Table 2.

TABLE 2

| SEQ ID NO: | SEQUENCE | TEMPLATE |
|---|---|---|
| 11 | CCCCACTGTGTTTAGC | HIV-1 GAG |
| 12 | CCTGGTGCAATAGGCCC | HIV-1 GAG |
| 13 | TTCCTGCTATGTCACTTCC | HIV-1 GAG |
| 14 | CCTTGGTTCTCTCATCTGG | HIV-1 GAG |
| 15 | TATCCCATTCTGCAGCTTC | HIV-1 GAG |
| 16 | TGCATGCACTGGATGCACTC | HIV-1 GAG |
| 17 | TGCATGGCTGCTTGATGTCC | HIV-1 GAG |
| 18 | ATTTGTTCCTGAAGGGTACTAGTAG | HIV-1 GAG |
| 19 | CTCATTGATGGTCTCTTTTAACATT | HIV-1 GAG |
| 20 | CCGAGTCCTGCGTCGAG | HIV-1 LTR |
| 21 | TTCAAGTCCCTGTTCGGGC | HIV-1 LTR |
| 22 | GCTGTGTGCACTTCAGCAAG | HIV-1 LTR |
| 23 | ACCTAGAGTGGTCTGAGGGA | HIV-1 LTR |
| 24 | CGAGTCCCTATTAACTTTCGCT | HIV-1 LTR |
| 25 | TCTCTAGTTACCAGAGTCACACA | HIV-1 LTR |
| 26 | GCCACTGCTAGAGATTTTTACACT | HIV-1 LTR |
| 27 | AGAACTTCTCTGGAACTTTCGTTTT | HIV-1 LTR |
| 28 | TTCCTGCCTTGGTTTCC | HIV-2 LTR |
| 29 | AGCGTGGAGCCGTCTGC | HIV-2 LTR |
| 30 | ACCGAATGACCAGGCGG | HIV-2 LTR |
| 31 | CAGGGTCTTGTTATTCAGGTGAAC | HIV-2 LTR |
| 32 | TTAACTTGCTTCTAACTGGCAGCT | HIV-2 LTR |
| 33 | CAAAGCAAGAAGGGTCCTAACAGAC | HIV-2 LTR |
| 34 | GACTAGGAGAGATGGGAACACACAC | HIV-2 LTR |
| 35 | TTATTAAGAGGTCTTTAAGCAAGCA | HIV-2 LTR |

Two stability studies were performed. In the first study, armored RNA templates were used at 100 copies per microliter in Tris.HCl (pH 7.0) containing 100 mM KCl. COPS corresponding to SEQ ID NOs: 11-35 were then added to the samples at a final concentration of 0 or 10 nM and the samples were incubated at 4° C., 37° C. or 45° C. for 15 weeks. RT-PCR with primers corresponding to the three RNA templates was performed using the conditions described in Example 3. The results of the study are shown in Table 3 and clearly demonstrates that the presence of COPS greatly stabilized both RNA templates.

TABLE 3

| Template | COPS Concentration | Temperature | Ct value (cycle number) | Cycle delay |
|---|---|---|---|---|
| HIV-1 GAG | 0 | 4° C. | 28.6 | N/A |
| HIV-1 GAG | 0 | 37° C. | 32.9 | 4.3 |
| HIV-1 GAG | 0 | 45° C. | 40.0 | 11.4 |
| HIV-1 GAG | 10 nM | 4° C. | 28.4 | N/A |
| HIV-1 GAG | 10 nM | 37° C. | 30.0 | 1.6 |
| HIV-1 GAG | 10 nM | 45° C. | 30.1 | 1.7 |
| HIV-2 LTR | 0 | 4° C. | 29.8 | N/A |
| HIV-2 LTR | 0 | 37° C. | 34.5 | 4.7 |
| HIV-2 LTR | 0 | 45° C. | No signal | — |

TABLE 3-continued

| Template | COPS Concentration | Temperature | Ct value (cycle number) | Cycle delay |
|---|---|---|---|---|
| HIV-2 LTR | 10 nM | 4° C. | 29.8 | N/A |
| HIV-2 LTR | 10 nM | 37° C. | 30.9 | 1.1 |
| HIV-2 LTR | 10 nM | 45° C. | 31.7 | 1.9 |

Figure 5:
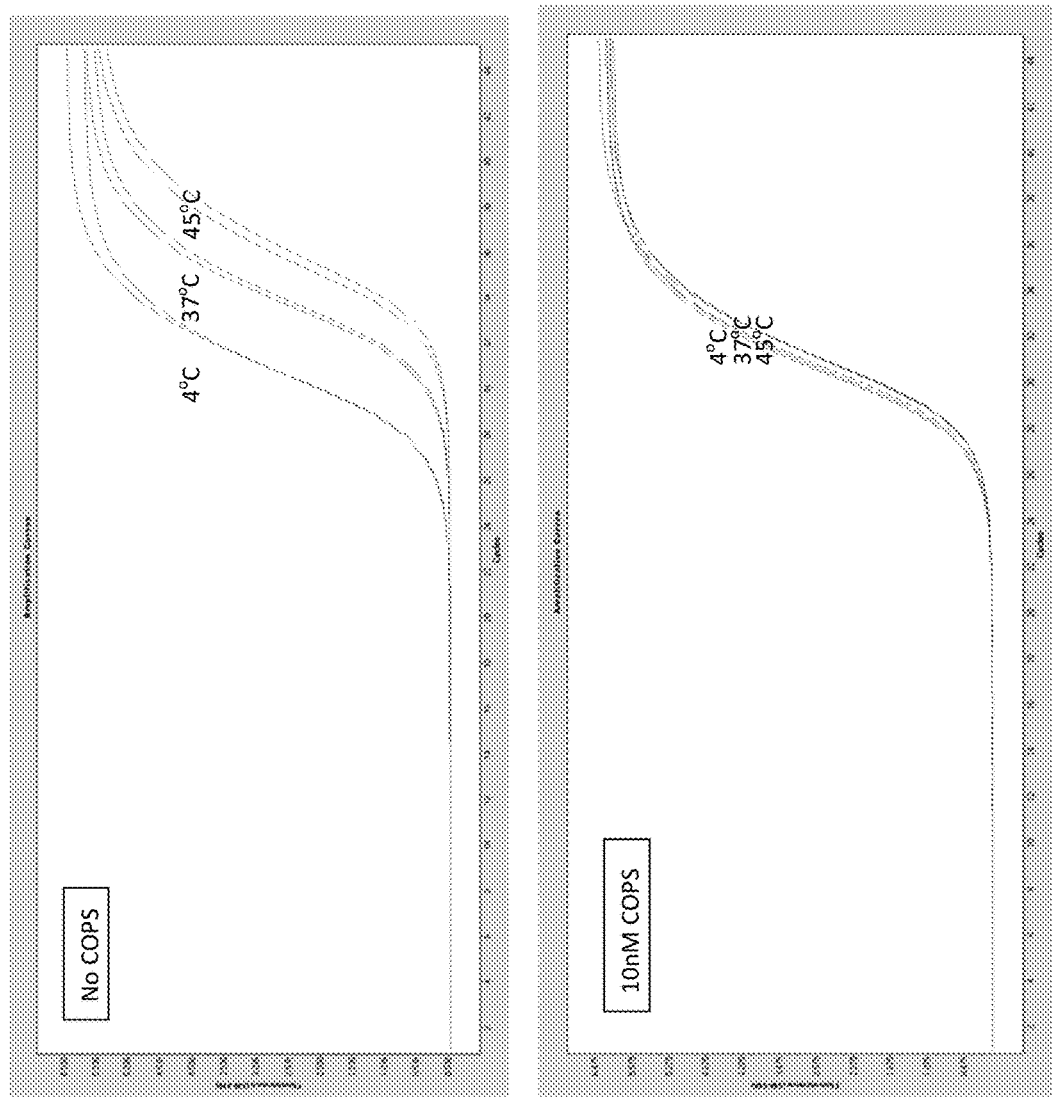
FIG. 5 shows the RT-PCR growth curves of a 71-day stability study of a HIV-2 LTR RNA transcript in the absence (TOP) or presence (BOTTOM) of complementary oligonucleotides. Samples were incubated at 4° C., 37° C., and 45° C., and amplified and detected by RT-PCR, where an increased cycle threshold (value) was indicative of sample degradation.

In the second study, unarmored HIV-1 and HIV-2 templates were used at 300 copies per microliters in the presence of 0 or 10 nM concentration of the corresponding COPS. The samples were incubated at 4° C., 37° C. or 45° C. for 71 days. RT-PCR with primers corresponding to the three RNA templates was performed using the conditions described in Example 3. The results of this study are shown in Table 4. FIG. 5 shows the RT-PCR growth curves generated for the HIV-2 LTR template. These experiments show that COPS can greatly increase the stability of both armored and unarmored RNA templates.

TABLE 4

| Template | COPS Concentration | Temperature | Ct value (cycle number) | Cycle delay |
|---|---|---|---|---|
| HIV-1 GAG | 0 | 4° C. | 27.3 | N/A |
| HIV-1 GAG | 0 | 37° C. | 30.6 | 3.3 |
| HIV-1 GAG | 0 | 45° C. | 32.9 | 5.6 |
| HIV-1 GAG | 10 nM | 4° C. | 27.0 | N/A |
| HIV-1 GAG | 10 nM | 37° C. | 27.4 | 0.4 |
| HIV-1 GAG | 10 nM | 45° C. | 27.7 | 0.7 |
| HIV-2 LTR | 0 | 4° C. | 27.5 | N/A |
| HIV-2 LTR | 0 | 37° C. | 30.5 | 3.0 |
| HIV-2 LTR | 0 | 45° C. | 32.4 | 4.9 |
| HIV-2 LTR | 10 nM | 4° C. | 27.3 | N/A |
| HIV-2 LTR | 10 nM | 37° C. | 27.7 | 0.4 |
| HIV-2 LTR | 10 nM | 45° C. | 27.8 | 0.5 |

The invention claimed is:

1. A method of preventing or reducing degradation of a segment of a single-stranded RNA template that is amplified in an amplification reaction, the method comprising the steps of:
   a) providing the single-stranded RNA template;
   b) hybridizing the segment of the single-stranded RNA template with one or more oligonucleotides whose sequences are completely or partially complementary to the segment of the single-stranded RNA template that is amplified; and
   c) reverse transcribing and amplifying the segment of the single-stranded RNA template under reaction conditions whereby the one or more oligonucleotides do not interfere with reverse transcription and amplification and whereby each one oligonucleotide from the one or more oligonucleotides is characterized by both being between 11 nucleotides and 50 nucleotides in length and having a melting temperature that is at least 5° C. lower than an extension temperature used during amplification, and wherein the sequence of each one oligonucleotide from the one or more oligonucleotides does not overlap with the sequence of another oligonucleotide from the one or more oligonucleotides; and the one or more oligonucleotides are present at a concentration that is at least fifty-fold lower than concentrations of primers and probes used during reverse transcription and amplification;
   wherein the one or more oligonucleotides comprise a group of oligonucleotides whose sequences consist of SEQ ID NOs: 1-10.

* * * * *

SEQUENCE LISTING

```
<160> NUMBER OF SEQ ID NOS: 35

<210> SEQ ID NO 1
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 1
tcacctcgcc ccga                                                       14

<210> SEQ ID NO 2
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2
gagttcgtcg ggccgc                                                     16

<210> SEQ ID NO 3
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 3
ggttgtgacc ggaacc                                                     16

<210> SEQ ID NO 4
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 4
tgcgcgtccc gttttga                                                    17

<210> SEQ ID NO 5
<211> LENGTH: 18
<212> TYPE: DNA
<213> ORGANISM: Artificial sequence
```

```
<220> FEATURE:
<223> OTHER INFORMATION: Synthetic oligonucleotide

<400> SEQUENCE: 5
ttttctagcg ttcgccca                                              18

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6 agggctttt tacgtgggag                                             20

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
tacttcgtaa cggtgcgggg t                                          21

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
ctcacttaat tgctggcgtc ag                                         22

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
cttcattctt gacatgtatg gcgc                                       24

<210> SEQ ID NO 10
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 10
ttatacagta ccaatcgtcg gttcg                                      25

<210> SEQ ID NO 11
<211> LENGTH: 16
<212> TYPE: DNA
<213> ORGANISM: Artificial sequence
<220> FEATURE:
<223> OTHER INFORMATION: Synthetic HIV-1 GAG oligonucleotide

<400> SEQUENCE: 11
ccccactgtg tttagc                                                16
```

<210> SEQ ID NO 12
<211> LENGTH: 17
<212> TYPE: DNA
<213> ORGANISM: Artificial sequence
<220> FEATURE:
<223> OTHER INFORMATION: Synthetic HIV-1 GAG oligonucleotide

<400> SEQUENCE: 12
cctggtgcaa taggccc                                                17

<210> SEQ ID NO 13
<211> LENGTH: 19
<212> TYPE: DNA
<213> ORGANISM: Artificial sequence
<220> FEATURE:
<223> OTHER INFORMATION: Synthetic HIV-1 GAG oligonucleotide

<400> SEQUENCE: 13
ttcctgctat gtcacttcc                                              19

<210> SEQ ID NO 14
<211> LENGTH: 19
<212> TYPE: DNA
<213> ORGANISM: Artificial sequence
<220> FEATURE:
<223> OTHER INFORMATION: Synthetic HIV-1 GAG oligonucleotide

<400> SEQUENCE: 14
ccttggttct ctcatctgg                                              19

<210> SEQ ID NO 15
<211> LENGTH: 19
<212> TYPE: DNA
<213> ORGANISM: Artificial sequence
<220> FEATURE:
<223> OTHER INFORMATION: Synthetic HIV-1 GAG oligonucleotide

<400> SEQUENCE: 15
tatcccattc tgcagcttc                                              19

<210> SEQ ID NO 16
<211> LENGTH: 20
<212> TYPE: DNA
<213> ORGANISM: Artificial sequence
<220> FEATURE:
<223> OTHER INFORMATION: Synthetic HIV-1 GAG oligonucleotide

<400> SEQUENCE: 16
tgcatgcact ggatgcactc                                             20

<210> SEQ ID NO 17
<211> LENGTH: 20
<212> TYPE: DNA
<213> ORGANISM: Artificial sequence
<220> FEATURE:
<223> OTHER INFORMATION: Synthetic HIV-1 GAG oligonucleotide

<400> SEQUENCE: 17
tgcatggctg cttgatgtcc                                             20

<210> SEQ ID NO 18
<211> LENGTH: 25
<212> TYPE: DNA
<213> ORGANISM: Artificial sequence
<220> FEATURE:
<223> OTHER INFORMATION: Synthetic HIV-1 GAG oligonucleotide

```
<400> SEQUENCE: 18
atttgttcct gaagggtact agtag                                          25

<210> SEQ ID NO 19
<211> LENGTH: 25
<212> TYPE: DNA
<213> ORGANISM: Artificial sequence
<220> FEATURE:
<223> OTHER INFORMATION: Synthetic HIV-1 GAG oligonucleotide

<400> SEQUENCE: 19
ctcattgatg gtctctttta acatt                                          25

<210> SEQ ID NO 20
<211> LENGTH: 17
<212> TYPE: DNA
<213> ORGANISM: Artificial sequence
<220> FEATURE:
<223> OTHER INFORMATION: Synthetic HIV-1 LTR oligonucleotide

<400> SEQUENCE: 20
ccgagtcctg cgtcgag                                                   17

<210> SEQ ID NO 21
<211> LENGTH: 19
<212> TYPE: DNA
<213> ORGANISM: Artificial sequence
<220> FEATURE:
<223> OTHER INFORMATION: Synthetic HIV-1 LTR oligonucleotide

<400> SEQUENCE: 21
ttcaagtccc tgttcgggc                                                 19

<210> SEQ ID NO 22
<211> LENGTH: 20
<212> TYPE: DNA
<213> ORGANISM: Artificial sequence
<220> FEATURE:
<223> OTHER INFORMATION: Synthetic HIV-1 LTR oligonucleotide

<400> SEQUENCE: 22
gctgtgtgca cttcagcaag                                                20

<210> SEQ ID NO 23
<211> LENGTH: 20
<212> TYPE: DNA
<213> ORGANISM: Artificial sequence
<220> FEATURE:
<223> OTHER INFORMATION: Synthetic HIV-1 LTR oligonucleotide

<400> SEQUENCE: 23
acctagagtg gtctgaggga                                                20

<210> SEQ ID NO 24
<211> LENGTH: 22
<212> TYPE: DNA
<213> ORGANISM: Artificial sequence
<220> FEATURE:
<223> OTHER INFORMATION: Synthetic HIV-1 LTR oligonucleotide

<400> SEQUENCE: 24
cgagtcccta ttaactttcg ct                                             22

<210> SEQ ID NO 25
```

```
<211> LENGTH: 23
<212> TYPE: DNA
<213> ORGANISM: Artificial sequence
<220> FEATURE:
<223> OTHER INFORMATION: Synthetic HIV-1 LTR oligonucleotide

<400> SEQUENCE: 25
tctctagtta ccagagtcac aca                                            23

<210> SEQ ID NO 26
<211> LENGTH: 24
<212> TYPE: DNA
<213> ORGANISM: Artificial sequence
<220> FEATURE:
<223> OTHER INFORMATION: Synthetic HIV-1 LTR oligonucleotide

<400> SEQUENCE: 26
gccactgcta gagatttta cact                                            24

<210> SEQ ID NO 27
<211> LENGTH: 25
<212> TYPE: DNA
<213> ORGANISM: Artificial sequence
<220> FEATURE:
<223> OTHER INFORMATION: Synthetic HIV-1 LTR oligonucleotide

<400> SEQUENCE: 27
agaacttctc tggaactttc gtttt                                          25

<210> SEQ ID NO 28
<211> LENGTH: 17
<212> TYPE: DNA
<213> ORGANISM: Artificial sequence
<220> FEATURE:
<223> OTHER INFORMATION: Synthetic HIV-2 LTR oligonucleotide

<400> SEQUENCE: 28
ttcctgcctt ggtttcc                                                   17

<210> SEQ ID NO 29
<211> LENGTH: 17
<212> TYPE: DNA
<213> ORGANISM: Artificial sequence
<220> FEATURE:
<223> OTHER INFORMATION: Synthetic HIV-2 LTR oligonucleotide

<400> SEQUENCE: 29
agcgtggagc cgtctgc                                                   17

<210> SEQ ID NO 30
<211> LENGTH: 18
<212> TYPE: DNA
<213> ORGANISM: Artificial sequence
<220> FEATURE:
<223> OTHER INFORMATION: Synthetic HIV-2 LTR oligonucleotide

<400> SEQUENCE: 30
accgaatgac caggcggc                                                  18

<210> SEQ ID NO 31
<211> LENGTH: 24
<212> TYPE: DNA
<213> ORGANISM: Artificial sequence
<220> FEATURE:
<223> OTHER INFORMATION: Synthetic HIV-2 LTR oligonucleotide

<400> SEQUENCE: 31
```

```
cagggtcttg ttattcaggt gaac                                          24

<210> SEQ ID NO 32
<211> LENGTH: 24
<212> TYPE: DNA
<213> ORGANISM: Artificial sequence
<220> FEATURE:
<223> OTHER INFORMATION: Synthetic HIV-2 LTR oligonucleotide

<400> SEQUENCE: 32
ttaacttgct tctaactggc agct                                          24

<210> SEQ ID NO 33
<211> LENGTH: 25
<212> TYPE: DNA
<213> ORGANISM: Artificial sequence
<220> FEATURE:
<223> OTHER INFORMATION: Synthetic HIV-2 LTR oligonucleotide

<400> SEQUENCE: 33
caaagcaaga agggtcctaa cagac                                         25

<210> SEQ ID NO 34
<211> LENGTH: 25
<212> TYPE: DNA
<213> ORGANISM: Artificial sequence
<220> FEATURE:
<223> OTHER INFORMATION: Synthetic HIV-2 LTR oligonucleotide

<400> SEQUENCE: 34
gactaggaga gatgggaaca cacac                                         25

<210> SEQ ID NO 35
<211> LENGTH: 25
<212> TYPE: DNA
<213> ORGANISM: Artificial sequence
<220> FEATURE:
<223> OTHER INFORMATION: Synthetic HIV-2 LTR oligonucleotide

<400> SEQUENCE: 35
ttattaagag gtctttaagc aagca                                         25
```